(12) United States Patent
Schlichting

(10) Patent No.: US 7,435,322 B2
(45) Date of Patent: Oct. 14, 2008

(54) DEVICE AND METHOD FOR AUTOMATICALLY ANALYSING THE CONSTITUENTS OF AN ANALYTE

(76) Inventor: Hartmut Schlichting, Tonwerkstrasse 9, Gilching (DE) 82205

( * ) Notice: Subject to any disclaimer, the term of this patent is extended or adjusted under 35 U.S.C. 154(b) by 815 days.

(21) Appl. No.: 10/467,552

(22) PCT Filed: Feb. 1, 2002

(86) PCT No.: PCT/EP02/01098

§ 371 (c)(1),
(2), (4) Date: Jan. 21, 2004

(87) PCT Pub. No.: WO02/061408

PCT Pub. Date: Aug. 8, 2002

(65) Prior Publication Data
US 2004/0112745 A1    Jun. 17, 2004

(30) Foreign Application Priority Data

| Feb. 1, 2001 | (DE) | ............................ 101 04 821 |
| May 6, 2001 | (DE) | ............................ 101 22 323 |
| May 29, 2001 | (DE) | ............................ 101 26 282 |

(51) Int. Cl.
*G01N 27/447* (2006.01)

(52) U.S. Cl. ................. 204/464; 204/614; 204/604; 204/610; 204/459; 204/462

(58) Field of Classification Search .......... 204/614, 204/464, 608, 457
See application file for complete search history.

(56) References Cited

U.S. PATENT DOCUMENTS 4,204,767 A    5/1980   Kato et al.
4,337,131 A    6/1982   Vesterberg
4,374,723 A    2/1983   Vesterberg
4,810,348 A    3/1989   Sarrine et al.
5,019,232 A *  5/1991   Wilson et al. ............... 204/469
5,234,559 A    8/1993   Collier et al.
5,275,710 A *  1/1994   Gombocz et al. ........... 204/461

(Continued)

FOREIGN PATENT DOCUMENTS

DE    2944127    5/1980

(Continued)

*Primary Examiner*—Alex Noguerola
(74) *Attorney, Agent, or Firm*—IP Strategies

(57) ABSTRACT

The invention relates to a device and a method for automatically analysing the constituents of at least one analyte, especially by means of gel electrophoresis and/or isoelectric focussing, comprising at least one separating matrix, especially a gel. Each separating matrix is applied on at least one side in a supporting direction S of a supporting element, can be loaded with an analyte, and can be electrically contacted on opposite ends in a separating direction T in order to split the analyte into its constituents. The invention is characterised in that the supporting element is embodied in such a way that it enables a material-transferring process to take place from one side—in an access direction Z which is different from the support direction S and the separating direction T—essentially over the entire area of the separating matrix in which the constituents of the analyte are located after being separated, and in that the supporting element comprises a continuous sealing surface which essentially prevents said material-transferring process from taking place outside said area.

13 Claims, 18 Drawing Sheets

U.S. PATENT DOCUMENTS

Figure 1:
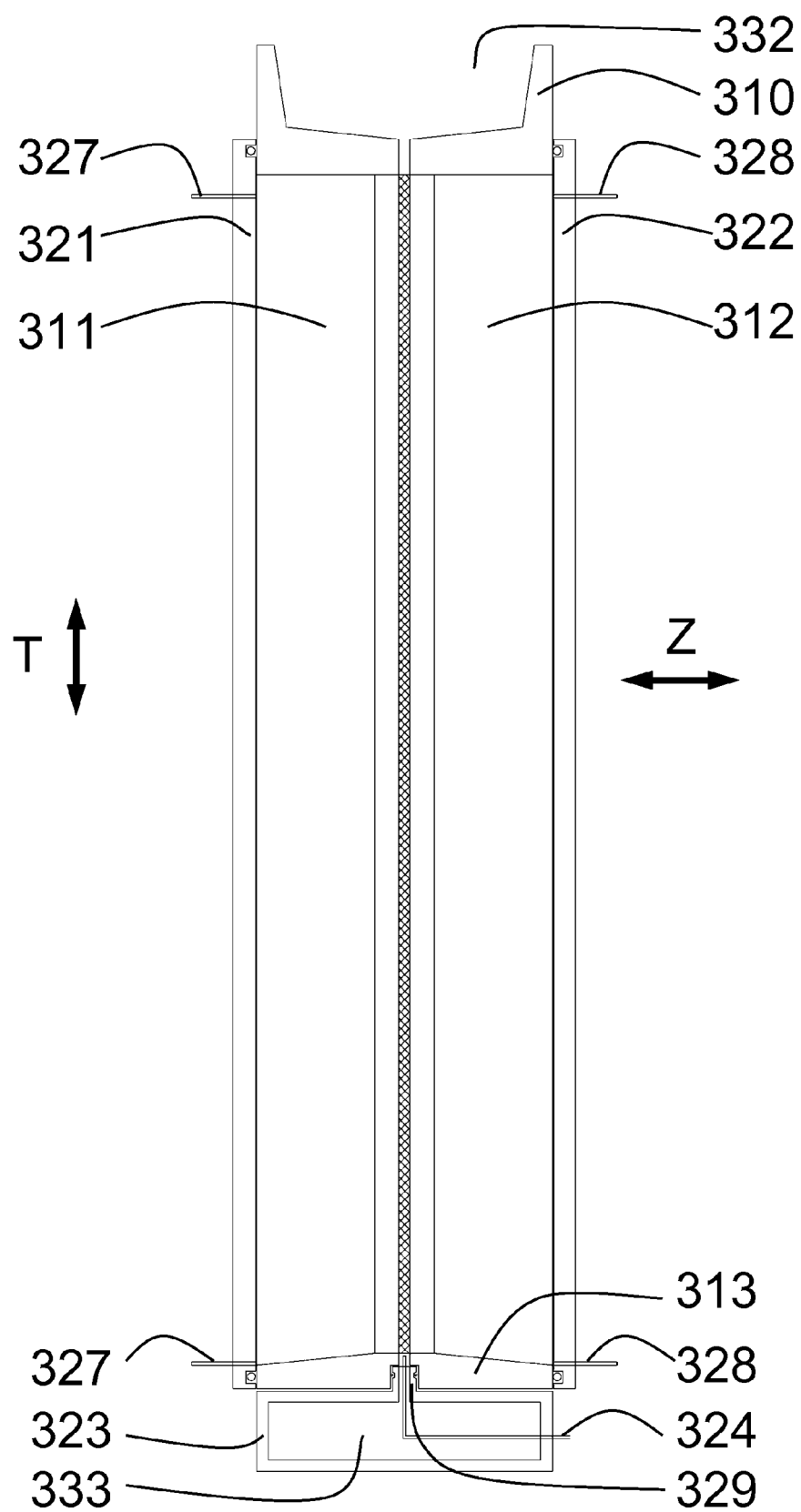

| | | | |
|---|---|---|---|
| 5,279,721 A | 1/1994 | Schmid | |
| 5,449,446 A | 9/1995 | Verma et al. | |
| 5,562,813 A * | 10/1996 | Mullaart et al. | 204/618 |
| 5,800,691 A * | 9/1998 | Kozulic | 204/466 |
| 5,954,931 A | 9/1999 | Maracas et al. | |
| 5,993,627 A * | 11/1999 | Anderson et al. | 204/456 |
| 6,171,463 B1 * | 1/2001 | Selby et al. | 204/456 |
| 6,201,628 B1 * | 3/2001 | Basiji et al. | 359/212 |

FOREIGN PATENT DOCUMENTS

| | | |
|---|---|---|
| EP | 0300924 | 1/1989 |
| EP | 0631132 | 12/1994 |
| JP | 02268272 | 11/1990 |

* cited by examiner

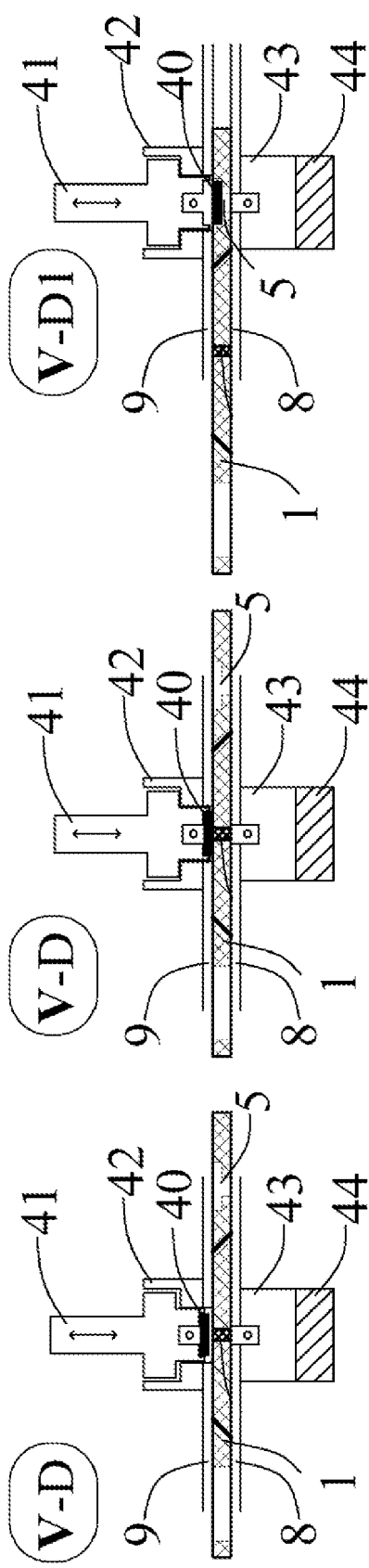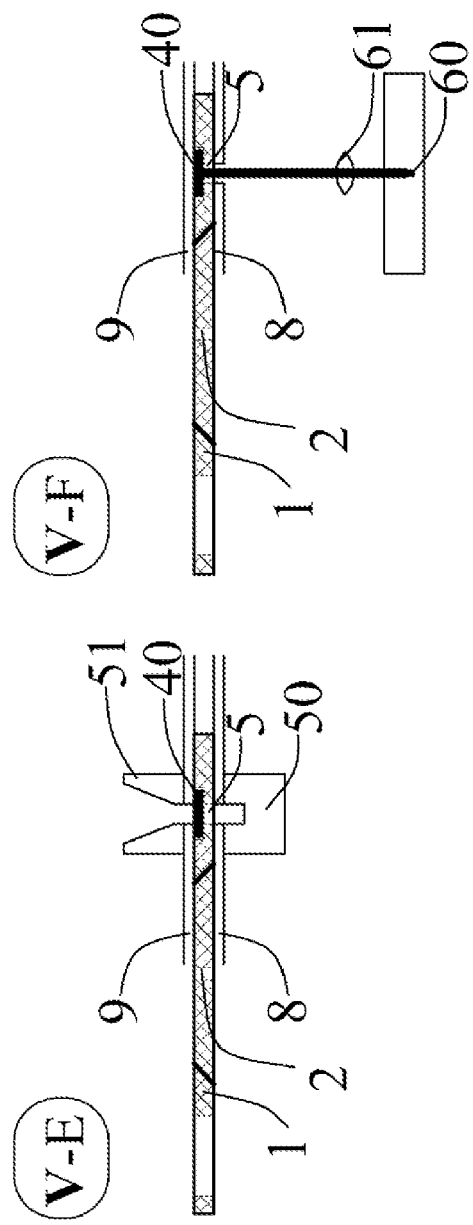
Fig. 16a Fig. 16b Fig. 16c Fig. 16d Fig. 16e

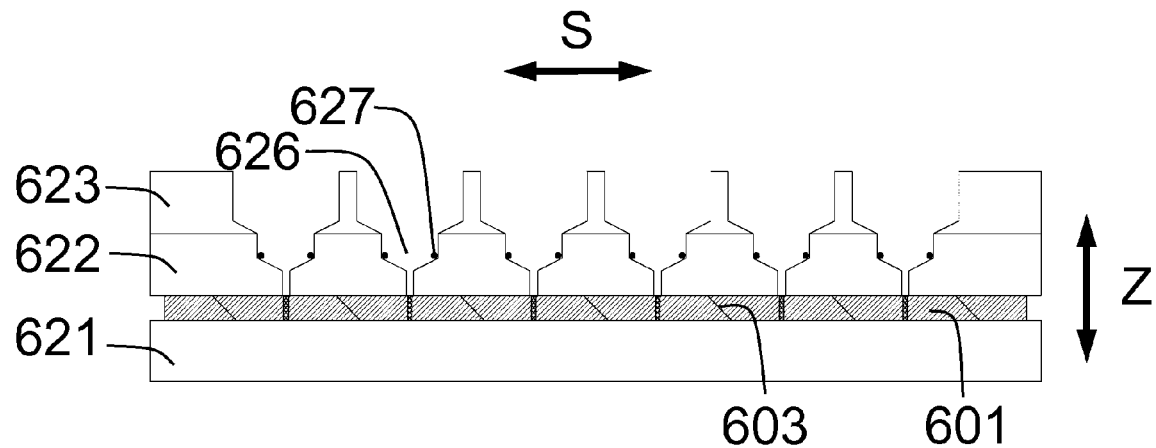
Fig.20 Station VI-T
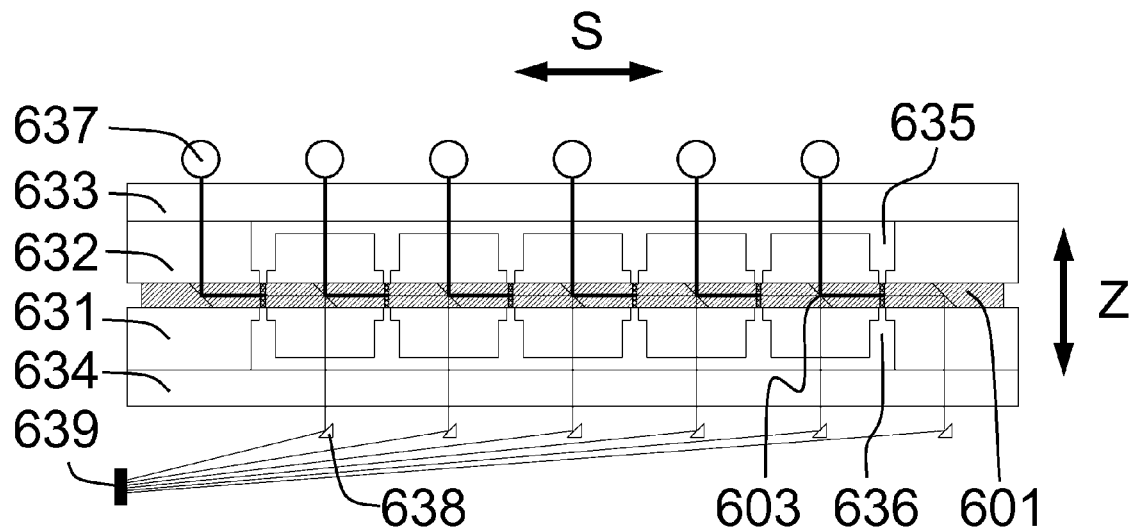
Fig.21 Station VI-F

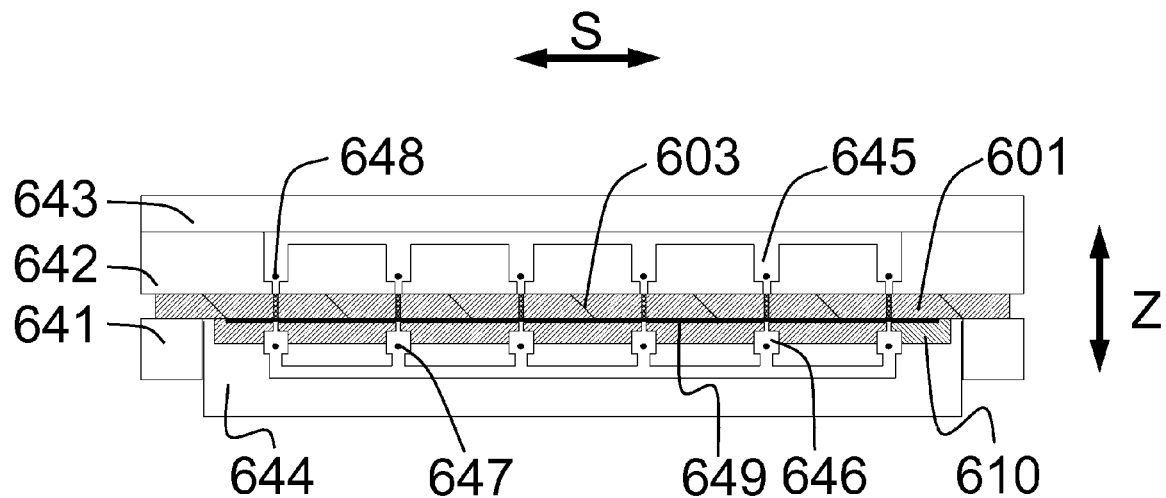
Fig.22 Station VI-B
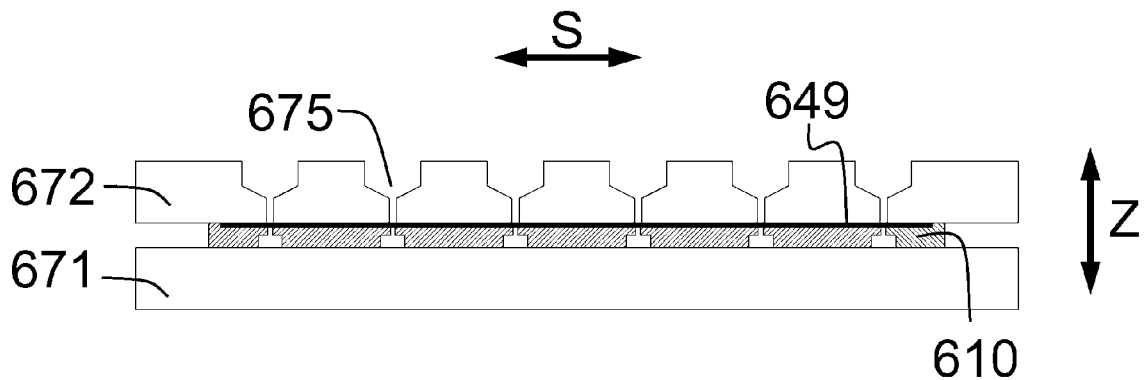
Fig.23 Station VI-R

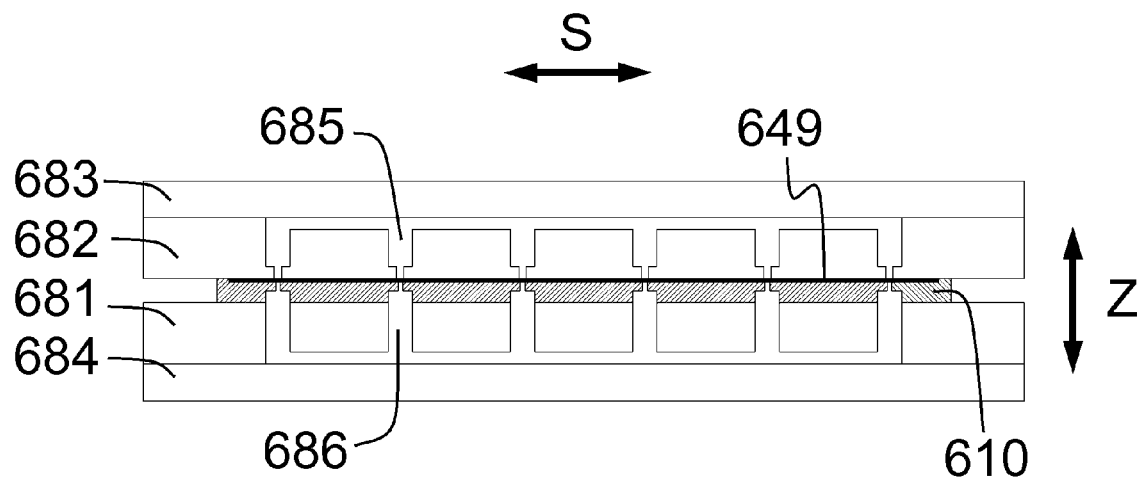
Fig.24 Station VI-W
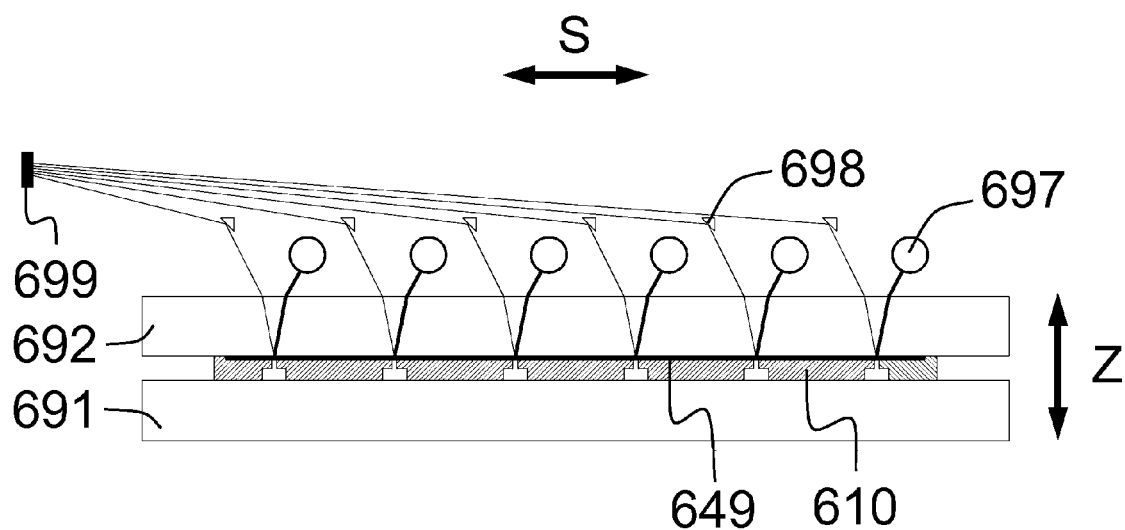
Fig.25 Station VI-D

DEVICE AND METHOD FOR AUTOMATICALLY ANALYSING THE CONSTITUENTS OF AN ANALYTE

The invention relates to a device and a method for automatic analysis of the components of at least one analyte, in particular by means of gel electrophoresis and/or isoelectric focusing with at least one separation matrix, in particular a gel.

Gel electrophoresis is an already established semi-quantitative method for the detection of single DNA fragments or proteins from a mixture of the same in an aqueous solution. Such a mixture is termed as analyte in the following, and as components of the analyte merely proteins are named, even if always DNA fragments and/or proteins or similar substances should be understood thereby.

During gel electrophoresis, the analyte is separated according to molecular weight of the involved proteins and is either detected with antibodies or simply is stained. Thereby, besides the molecular weight, also the charge and the shape of the substances play a role. For separation, the analyte is applied locally onto a separation matrix which is moistened with an aqueous buffer solution. Common matrices are agarosic gels and poly acryl amide gels of different concentration. The analyte is applied at one end of the separation matrix. By applying a voltage of e.g. 50-2000 V, it is subsequently moved within the separation matrix in the direction of the voltage. The aqueous buffer thereby serves for maintaining the pH-value and the salt concentration. According to their molecular weight, shape, and charge, the proteins thereby are retained differently strong by the matrix and distribute themselves after some time (e.g. 1-10 h) within the separation matrix along the current path.

The proteins thus separated are subsequently identified by means of a biological chemical reaction with antibodies. This occurs in a specifically prepared membrane which takes up the separated substance. In most cases nitro cellulose or nylon are used. The transfer from the separation matrix results by applying voltage, and, in fact, extensive between the separation matrix and the membrane pressed there upon. This is called blotting. For acceleration, this can be supported by a pressure difference. After a while, strongly depending on the blotting conditions, the charged proteins have shifted into the membrane quantitatively. By adding a specific antibody, a certain protein then is bound in the protein mixture selectively. The antibody is detected in most cases by means of radio active, fluorescence or chromatic labeling and thus makes the protein identifiable ("visible").

If the position of the proteins within the separation matrix after the separation has already been determined in preliminary tests, it is sufficient to stain the proteins unspecifically. This occurs by dipping the whole separation matrix into a staining solution, which preferentially stains proteins. The separation matrix subsequently is again destained. Bands remain visible, indicating the current position of the proteins on the separation matrix. The position of the bands is a rough measure for the molecular weight of the proteins, the intensity of the bands is a rough measure for the amount of proteins present in the substance to be measured. As detector within the optical field, on the one hand serves the appearance, on the other hand a calibrated densitometer, registering the intensity of the stain. The staining step subsequent to the separation can be omitted, if the analyte has been treated with a suitable stain prior to separation. For this, mostly fluorescing stains are used, which subsequently are detected automatically by means of UV-scanners.

For the first step—the electrophoretic separation—several arrangements are established:

During vertical slab electrophoresis, typically 10-50 different analytes are applied in a very broad gel (50-150 mm long, 100-200 mm wide, 0.3-2 mm thick) side by side. They run parallel, but in separated paths. The gel commonly first lies between 2 glass- or plastic plates, as long as a voltage is applied. 2 reservoirs with buffer solution communicate respectively with the upper and lower end of the gel. After separation of the proteins, the gel with the glass plates is taken out of the device, the glass plates are removed, and the staining steps and the further transfer steps, respectively, are carried out for blotting. The gel is extremely instable mechanically: it can tear by its own weight, sucks onto plane basis and buckles immediately. Without a buffer solution it dries, and thereby modifies its shape. Because of this, the automatic handling of the gel without the supporting glass plates is impossible. At present 6 different appliances are common to support the above-mentioned processes: an apparatus for pouring of the gels, a separation chamber, a power supply, staining vats, and a densitometer. In case an immune reaction is carried out, additionally a blotting apparatus is required as well as further staining and buffer exchange vats.

By means of staining of the proteins prior to electrophoresis, one can achieve that the evaluation procedure can result without removing the glass plates. Thereby, a partial automation is possible with restrictions in the staining technique. The blotting process thereby cannot be automated.

During sub-marine electrophoresis, the gel lies on a horizontal plate which is lying in the vat. The vat is filled up with buffer up to slightly above the upper edge of the gel. The two electrodes are respectively arranged at the end of the gel in the buffer. For staining, evaluating and blotting, the gel is taken out of the vat. Also here, automation is not easily possible.

During the horizontal slab electrophoresis, the gel lies on a horizontal glass plate and is exposed topside. The buffer is provided to a limited extent from correspondingly thickened gel blocks at both ends of the gel. Here, in fact already partial automation is possible. The upside exposed gel enables staining after the separation. Also, a UV-scanner can have direct access to the gel. Blotting without removing the gel, however, is also not possible with these appliances, because for blotting, the gel has to be electrically contacted from both phases and additionally has to be in contact with a membrane from the exposed face. An electrode on the lower side of the gel would, however, render the $1^{st}$ electrophoresis step impossible, because the applied voltage would be short-circuited. Blotting methods, solely based on diffusion, last too long.

With all methods using an extensive/flat gel and having several analytes running simultaneously, besides handling problems, the following further problems occur:—heat development due to the supplied electrical energy leading to different running periods at the edges and in the middle of the gel plate. Cooling by means of air or the carrier plate should provide remedy here. In case large glass plates are used, the gel often has a different thickness in the middle or at the edge, influencing the running velocity. Attempts to remove this are mechanical supports. Narrow placed paths can influence themselves mutually. An attempt to encounter this is sufficient spacing or separation of the path by means of grooves in the glass plate lying underneath. For loading special pipettes and loading slots are used to avoid errors caused by spacing which are too small. With horizontal gels, a shifting of the chemical environment during electrophoresis occurs due to the limited reserve of buffer, influencing additionally the running velocity.

Rod electrophoresis is a variant according to which the gel is enclosed in a glass tube. Here, prior to electrophoresis, staining is carried out. By this, automation, in fact, becomes possible easily; however, only as long as blotting is abandoned. For blotting, with sufficient diameter of the tube, the gel can be taken out by means of a piston. Due to the mentioned poor mechanic characteristics of the gel, unloading is a very hazardous procedure which, even if it succeeds, delivers poor reproducible results. Total automation thus is possible neither.

For capillary electrophoresis, a very thin and long capillary (e.g. 0.1 mm×50 cm) is used. The dimensions allow for a very high resolution of the molecular weight, improving with decreasing cross section and increasing length. The capillary is filled with gel automatically which is removed after the procedure by means of water under high pressure. With suitable capillary geometry, the gel can be omitted. The stain is applied during loading of the analyte. The substances are detected with an UV-scanner during passing a certain position in the capillary. This variant, therefore can be carried out automatically very well with respect to the detection of the different molecular weights. By a high number of capillaries, at the same time, a high throughput can be achieved. Blotting, however, is impossible with capillary electrophoresis, because the access to the gel from the side is impeded.

With capillary electrophoresis, the very high voltage (up to 30,000 V) and the heat development and the stability of the capillary are problematic. The surface specific heat development increases with the diameter and even stronger with the length of the capillary. This is encountered by cooling with air and water.

To take account of the problematic that proteins of different composition but identical molecular weights have similar running velocities in the gel, modifications of the electrophoresis were developed, which, however, as explained in the following, are not automated due to their complicated handling:

The gradient gel. The acryl amid concentration in the poly acryl amide gels substantially influences the running velocity of the proteins. Therefore, normally the concentration is complied with as exactly as possible. The concentration, however, can be consciously varied along the running direction of a slab gel, to achieve that high and low molecular weights of the proteins will be displayed well separated on the same gel.

The Ferguson gel. Besides the molecular weights, the different shape of the proteins influences their running velocity. This can be taken advantage of by using gel matrices of different pore size. If the concentration of the gel is varied transverse to the running direction and the same analyte is applied in all paths, then a Ferguson-plot is generated. In the two-dimensional image, proteins are represented by curves of different gradients. Due to the fact that two different characteristics of the proteins are detected this method is considerably more informative as the standard electrophoresis.

The isoelectric focusing. Thereby, as further characteristic, the isoelectric point of the proteins is retrieved. A pH gradient along the gel channel is generated in the gel. The analyte is applied at an arbitrary point, preferentially in the middle of the gel channel, and voltage is applied. Because only at the position with the matching pH-value, the charge of the proteins disappears, the proteins drift until they have reached this point and remain there. After sufficient time, an arrangement of the proteins in the gel is reached corresponding to their isoelectric point, which thereby is determined.

2D electrophoresis. This is a combination of isoelectric focusing with standard electrophoresis. In a first gel, mostly a rod, the proteins are separated according to their isoelectric point. The thus separated proteins are transferred to a second gel—a slab gel—and there they are further separated electrophoretically. Thus, a two-dimensional fingerprint of the analyte is obtained. In one dimension, there is the isoelectric point and in the other direction, the molecular weight is plotted.

At present, methods are established copying a "laboratory on the chip". These methods comprise techniques for the transfer of substances within the chips, for reaction with added reagents and for detection, including also mass spectrometry in vacuum.

As premise, these methods have the automation in small dimensions, and they try to carry out all known biochemical methods on this micro scale. In a carrier, mostly a translucent glass plate of e.g. 40×10 mm and 1 mm thickness, at least one channel of e.g. 5-50 μm is recessed. This channel is closed at the top enduringly with a cover plate lying on the lower chip, whereby a closed channel having very small dimensions is built up. The electrophoresis takes place in this channel which firstly is filled with a carrier matrix, mostly a special gel with low viscosity. The contact results from top side through fine openings in the cover plate, through which the analyte is applied also. The evaluation results likewise to the capillary electrophoresis, in that the separated proteins pass by a detector. Thereby, mostly an optical detector is concerned, accessing from top side through the planes of the translucent glass plates. The adequate stain substances are added prior to the beginning of separation. Through side channels, running into the main channel, it is possible to pass through several analytes in the same channel subsequently and to analyze them in the separation matrix. Principally, also immune reactions can be carried out in that adequate reagents are passed through from one of the side channels. Hereby, the transport is carried out by adequately applied voltages. However, thereby the point of time has to be known, at which the reagents can be supplied meaningfully, because only one reaction with the part of the main channel prior to the channel outlet takes place at any time.

For carrying out a comprehensive immune reaction, as they have been carried out in the already explained methods, it would be necessary, to bring immune reagents into contact with every part volume leaving the separation channel, and to evaluate the reaction. Such an immune reaction can comprise e.g. 5 or 10 biochemical steps, taking time respectively. Due to constructional reasons, these reactions come up sequentially, the screening of all separated components there is time consuming accordingly, in spite of the reaction velocity increased by the small size. As long as no knowledge concerning the molecular weight and therefore the running time of a protein searched for exists, therefore, only by means of many experiments, the "reactive position" searched for can be determined or in that conventional electrophoresis with blotting and immune detection is carried out first.

Therewith, the present chip constructions are no full substitute for conventional blot-techniques in spite of their high degree of automation, allowing for the transfer, and thus the immunologic detection of all separated substances simultaneously in one production step.

Accordingly, the object of the invention is to provide a device and a method for automatic analysis of the components of at least one analyte which, avoiding the drawbacks mentioned above, allow for an automatic gel electrophoresis including transfer of the separated analytes to a membrane or a further gel.

This object is solved by a device and a method, respectively, according to the independent claims. Further embodiments are defined in the dependent claims.

According to the invention, a device for automatic analysis of the components of at least one analyte, in particular by means of gel electrophoresis and/or isoelectric focusing, with at least one separation matrix, in particular a gel, is provided whereby each separation matrix 602 is supported on at least one side in a support direction S by a support element 601 such as a sample plate, is loadable with an analyte 626, and is electrically contactable at opposing ends 627, 628 in a separation direction T for separation of the analyte into its components, characterized in that the support element 315, 215, 102, 1, 601 is formed such that it allows for a mass transfer process from one side and, in fact, from an access direction Z, differing from the support direction S and the separation direction T, substantially over the entire area of the separation matrix 314, 214, 101, 2, 602, in which the components of the analytes after separation are contained, and the support element 315, 215, 102, 1, 601 has a continuous sealing face, preventing substantially this mass transfer process outside this area.

Thereby, it is achieved advantageously that the unstable separation matrix together with the separated components of the analyte can remain subsequent to the separation process within the robust support element, to be subjected to a plurality of process steps. By means of the one-sided access in access direction, it is possible to carry out mass transfer processes with each of the separation matrices separately, e.g. to stain, to de-stain, to change the buffer, to transfer the separated components of the analyte by diffusion onto a membrane. The band pattern can be read out in reflection. The pouring and loading of the separation matrices is also possible. Thereby, continuous sealing of the accesses enables automatic operating sequences.

In a preferred embodiment of the invention, the support element 315, 215, 102, 1, 601 can be formed such that it enables a mass transfer process from both sides in the access direction Z, respectively, subsequently over the entire area of the separation matrix 314, 214, 101, 2, 602, in which the components of the analyte are contained after separation, and the support element can have on both sides in the access direction (Z) respectively a continuous sealing face, preventing substantially the respective mass transfer process outside this area. By this additional access from the $2^{nd}$ side, the efficiency of the mass transfer processes is essentially improved, the blotting process on a membrane can be substantially accelerated by current and pressure differences, the transfer onto a further separation matrix is enabled, and the band pattern can be read out in transmission. By this, all process steps occurring during the gel electrophoresis and the isoelectric focusing are possible at the separation matrix, and thus, can be automated while the separation matrix remains within the protecting and sealing support structure.

The invention also comprises the corresponding method for automation of the analysis of the components of at least one analyte as well as a device for transportation of substances between processing stations.

All embodiments of the invention have in common that each of the analytes to be investigated is analyzed in a single element. By combining many of such elements, it is possible to investigate as many sample substances simultaneously as desired. Subsequently, if desired, the familiar image of the parallel analysis as in a slab gel can be generated in an electronic manner, with which, also in chemical and biological respect, full consistency exists.

A further idea of the invention is that the separation matrix is very narrow in Z-direction and is free laterally over the complete length for staining, de-staining, blotting and for transfer of the separated analyte in a further separation matrix. Due to the small width of the access in Z-direction it is ensured that the support element, being adjacent from the S-direction, in fact stabilizes the mechanically instable separation matrix.

A further idea of the invention is that the optical evaluation of the stained components of the analytes can result either in S-direction and/or in Z-direction. Thus, either the optical distance within the gel can be made large, to increase the sensitivity, and the support elements can be made cheaper, because the optical elements are omitted or prior stained proteins can be observed during the separation.

A further idea is that the directions T, S and Z are respectively perpendicular with respect to each other whereby it is possible to separate the analyte within the separation matrix in T-direction, and in Z-direction to enable access for biochemical, chemical, or physical reactions or for transfer of the separated analyte on the complete length, and in S-direction, to guarantee by means of suitable support elements, the stability of the separation matrix and, if the support elements are translucent, simultaneously optical access. Thus, the removal of the mechanically instable gel from the support elements is unnecessary, and the possibility exists to completely automate all process steps including the blotting procedure over the entire gel length.

In the following the invention describes a new variant of the gel electrophoresis combining the advantages of the known processes, without having new drawbacks. By means of the device according to the invention, it is enabled to combine the entire procedure—the pouring of the gel, the applying of the sample substance, the electrical separation of the proteins, the staining and de-staining, the optical evaluation as well as the blotting of all separated substances—within one apparatus. Except for the loading of the analyte—principally this can also result automatically—no manual interferences are necessary until the result is available, in common manner electronically. In case the apparatus is used for a blotting procedure, also the insertion and removal of the membrane is ensued, which can also be automated. By small dimensions of the gel paths as well as active temperature stabilization during some or all process steps, very fast and precise results are possible. The method can be carried out in parallel working in any way whereby a very high throughput becomes possible. Nothing has to be changed in the chemical procedure of the established slab gel electrophoresis—the gels, the stains, the labeling, the buffers. The blotting procedure also is carried out under the conventional chemical conditions on the same membrane materials. Therefore, new measured values are compatible with conventionally determined measure values, and the existing data stock remains compatible with the use of the new apparatus. The invention therefore replaces several of the apparatuses used up to now, shortens the time until a result is available, and, therefore, increases substantially the throughput. Due to omitting human interventions, the total procedure can be easily validated, is practically not influenced by individual handling of different operators, and is reliable and suitable for constant use.

For the investigation of DNA-fragments, the staining step also results automatically. This is of particular importance because thereby usually as stain ethidium bromide is used. This substance is strongly mutagen; therefore contact with the skin has to be avoided strictly. Therefore, automation is especially important.

The direction in which the proteins are separated, depends on the embodiment and results e.g. from top to bottom (T-direction), the proteins are subsequently stained from left to right (Z-direction), again de-staining and eventually are evaluated optically from front to back (S-direction). In case blotting is carried out, this results from left to right (Z-direction). Each other initial position is of course possible; essential is the definition of the directions T, Z, S.

According to the invention, therefore the optical evaluation and also later the blotting in the same arrangement can result. After the blotting, one embodiment additionally allows for the immune detection within the blotting membrane. Thus, in the separation matrix all 3 dimensions are used, and it is possible to leave the support elements connected to the separation matrix during the whole procedure. The blotting procedure therefore is fully automated because the critical step of the stripping of the separation matrix from the support elements is omitted.

The electrophoretic currents, voltages and times which are used for optical investigation of the analyte, can be adapted unchanged for the immunologic investigation of the analyte, whereby an unambiguous assignment of the results is possible.

As detector any sensor element qualifies, responding to the characteristics which characterize the position of the different proteins:

For example, CCD-array of a CCD-camera, in case that the light source illuminates the entire length of the gel channel simultaneously, a single photo diode with appropriate collector, in case the light source scans the gel channel, a film or semiconductor array sensitive to radio activity, in case the gel is labelled radio active instead of the staining procedure, a detector for fluorescent radiation, in case the staining is carried out with a fluorescent active stain, a pH-sensitive sensor, mechanically sensing the channel.

As light source in a broad sense, all sources can be considered, the emission of which is influenced with or without a preceding pre-treatment by the proteins in reflection or transmission. These are amongst others a filament lamp with or without focusing, an array of light emitting diodes with or without focusing, a laser expanded or not, a UV-light source with or without focusing, an infrared light source with or without focusing, a radio active source.

To enable a good coupling of sensor and detector to the limiting glass plates, it can be meaningful, to flood this volume with an appropriate liquid. Thus, a liquid having a similar index of refraction as the glass plate or the gel can prevent reflections and can compensate for damages of the surfaces.

In one embodiment, the matrix channel is substantially longer in T-direction than it is wide in S-direction and deep in Z-direction, and has a rectangular cross section. It is open and accessible in Z-direction and is covered in S-direction by means of thin glass plates. In Z-direction, the thickness of the separation matrix is sufficiently small, to enable the effective diffusion of stains. In S-direction, the thickness of the separation matrix is sufficiently small, to enable the heating and cooling of the separation matrix and its temperature control through the thin glass plates. The temperature control of the separation matrix enables the acceleration of the diffusion of the stain/de-staining liquids as well as control of thermally instable substances. The gel channel is fixed to a supporting structure together with the glass plates. Such an arrangement is termed as "stick" in the following.

A stick can be manufactured at very low costs, e.g. as injection molded plastic part. The stick can be thrown away after the measurement; the gel never has to be removed therefrom. Therefore, the gel can be as instable mechanically nearly arbitrarily.

As alternative for glass plates all types of foils or plates can be considered which are translucent for the radiation used, in particular the same materials which are listed in the following embodiment for the analyzing plates. With sufficient stability of the gel, also one of the covers can be omitted.

According to the stability of the gel used, it can be useful to slightly reduce the access to the gel in Z-direction directly at the gel, to avoid that the gel is displaceable laterally. Also coatings for an increase of the adhesion of the gel channel to the glass plates are possible.

In a further embodiment, instead of a complete opening of the gel channel in Z-direction, a partially but continuous opening of the gel channel, however, still over the entire length (T-direction) is used. This can be done in that one capillary having a substantially circular cross section is provided with a high number of small openings on opposing sides. These openings can have macroscopic as well as microscopic dimensions. Through these, the staining and de-staining substances can reach the gel just as well as in the case of a complete opening. Also blotting is possible. According to this embodiment, the non-perforated sides of the capillary correspond to the S-direction. Thereby, it can be useful, to shape the capillary oval, to avoid problems with the refraction index in the optical path.

The main apparatus for handling of these sticks is provided with its own evaluation sensor mechanism and corresponding staining and de-staining means for each stick. Thereby, the stick can remain at the same place in the apparatus during the whole procedure rendering the main apparatus very simple. By combining an arbitrary number of sticks and the also relatively cheap sensor mechanism, any number of substances can be measured simultaneously, equivalent to the typical 10-20 paths of the slab electrophoresis. The individual sensor mechanism, however, is not compulsory, also a common evaluation means, to which the single stick can be transported, can be meaningful or a sensor, sampling the sticks sequentially.

In a further embodiment, a number of fixedly mounted gel channels which can be automatically filled up with gel, is standing in the main apparatus, in that the channels at first being laterally open, are sealed on both sides and subsequently are released. By pressing of a membrane, besides the separation and stain steps, blotting also is possible.

A further idea of the invention is to build the support elements in S-direction such that it is possible to carry out many different working steps by means of different parts of the main apparatus at a separation matrix in that only the support elements are displaced laterally, preferentially in S-direction. The gel channel, thus, no longer is stationary between different process steps but rather is transported to a new position for carrying out each new procedure by a very simple mechanism:

For this purpose, in one embodiment a penetration having the dimensions of the gel is cut through a glass plate. This glass plate is two-dimensionally enclosed between two further glass plates from its top and from the bottom, providing for the sealing. The two glass plates are stationary, while the middle glass plate can be moved transverse with respect to the direction of the penetration, i.e. of the gel channel. The middle glass plate with the gel channel is termed as sample plate in the following; the two external plates are termed as analysis plates.

By a displacement mechanism the sample plate can be brought into several discrete positions relative to the stationary analysis plates, which are termed stations. In each of the stations, a special procedure can be carried out with the sample plates. Typical examples for procedures are: pouring of the gel—applying of the sample substance and electrophoresis-staining, de-staining of the gel and detection of the bands—blotting-immune detection—2D electrophoresis— transfer to a further separation matrix—cleaning of the gel channel. For this purpose, corresponding devices are provided at the analysis plates at each station.

During the individual process steps, the sample plate can be moved pressure-free during the displacement between the analysis plates. In the working position, the analysis plates are pushed against the sample plate whereby the gel channel is completely sealed at the top and at the bottom, if no corresponding station in the analysis plates is accessing. The processing of the gel mainly is carried out in the stations in Z-direction transverse to the displacement direction. Preferentially, the upper analysis plate is mounted flappable, to allow for a very simple maintenance of the sample plate.

In one embodiment, pouring is carried out in station (V-A) through 2 openings in the lower analysis plate. The sample substance is applied into the station (V-B) through a small funnel which is attached onto the upper analysis plate. Together with a second funnel, in this position also the buffer is brought into contact with both gel ends and the electro analysis is carried out. In station (V-C) the staining is carried out by small chambers which communicate via slots in the two analysis plates from Z-direction with the gel. In this station also the band pattern is read out from S-direction. For this, one respective mirror is arranged in the sample plate on both sides next to the gel channel, allowing for an optical path in the direction perpendicular to the sample plate. The optical path e.g. starts at a light source below the analysis plate, runs through the gel, and is deflected in a detector, for example underneath the analysis plate. In station (V-D) it is possible to blot the proteins in Z-direction from the gel by means of current onto the membrane. For this, below the lower analysis plate, a chamber with buffer and electrode, and above the upper analysis plate, a further chamber with a removable membrane, which is pushed onto the gel is present. The latter also is mixed with buffer and contacted electrically. In station (V-E) the readily blotted membrane which previously was deposited on the sample plate, is brought into contact with immune reagents and in station (V-F), this membrane is analyzed. In a further station (V-X) which is not illustrated, the gel channel is brought into contact with a second gel, being perpendicular to the upper analysis plate. The $2^{nd}$ two-dimensional gel allows for electrophoresis in a direction perpendicular to the original direction. For this, beneath the analysis plate, a chamber is arranged, containing the buffer and an electrode. The two-dimensional gel also is equipped with a buffer chamber and an electrode at its opposing edge. In position (V-R), the rinsing of the gel from the channel and its cleaning is provided for. In the sample plate, for this two further short channels are provided perpendicular thereto, independently from the gel channel. The gel which is polymerized after pouring into the inlets and outlets can thus be rinsed via adequate openings in the analysis plate.

A further plate for the supply capillaries to the funnels, a mechanism for pressing of the upper analysis plate, for pressing of the sample well plunger, for pressing of the blotting plunger, for pressing of the $2^{nd}$ gel during the 2D electrophoresis as well as for the electrode supplies can be attached above the upper analysis plate.

In a further embodiment, besides the access as it results in station (V-C) and (V-E) simultaneously on the entire length of the gel channel and/or the membrane, an access results on the selected part sections, to save reagents (not shown). Therefore, the slots are necessary in the analysis plates which comprise only a part of the full channel length. In the extreme case, this can be a punctual opening.

In a further embodiment, the reading out of the band pattern from Z-direction results in that for this, a further station is provided. The optical mirrors are omitted. Therefore, in the case of transmission measurements through the separated and stained proteins in the gel, the optical absorption is increased against the detection from S-direction, because the optical path in the gel is increased. With diffuse radiation from the band pattern, the steradian effective for the detector is increased, because the distance to the lens can be decreased. Thereby, smaller amounts of proteins can be detected. These advantages also persist for an application of non-optical detector methods. Further, the distance between the gel channels can be reduced, and their number can be increased. The optical path can be widened adequately by means of lenses, to guarantee a better utilization of a CCD-array. For the manufacturing of this sample plate, no high quality optical components and phases are necessary. The sample plate can be manufactured at extreme low costs, for example as a slotted plastic injection molded part.

In a further embodiment, the reading out of the band pattern from a direction lying between the S-direction and the Z-direction is carried out e.g. at 30 degrees, seen from the S-direction. The optical mirrors are omitted. The refraction index of the sample plate is selected adequately, to hit the channel under a preferably advantageous angle.

In a further embodiment, the transport of the membrane results by means of an additional membrane plate instead of the sample plate. The sample plate then comprises a number of channels; preferentially one for each separation matrix and the membrane plate comprises a number of grooves, preferentially one respectively, for the deposit and transport of the corresponding membranes after blotting.

In a further embodiment, the membranes assigned to the channels are not separated but rather form a large continuous membrane. In this case blotting results simultaneously from all channels on separated paths of this membrane. The membrane plate for transport of the membrane comprises a groove for receiving the whole membrane.

In a further embodiment, the continuous membrane is situated on a movable plunger underneath the blotting station (VI-D). In this station, in which at first blotting was carried out from the sample plate, after displacing the sample plate, all steps of liquid supply to the membrane can be carried out (also multiply), in particular buffer exchange, loading with immune reagents, rinsing, washing, cleaning, carrying out reaction. The detection of the resulting reaction is carried out by means of a detector plate which is slid laterally over the membrane, preferentially from the opposing side as the sample plate.

In a further embodiment, in this station (VI-D) additionally the reading out of the membrane is enabled by means of a laterally inclined arrangement of the detector components or liquid supplies.

In a further embodiment, at least one penetration is accommodated transverse to the direction of the separation channels in the sample plate. In this transverse channel, the analyte can firstly be separated by means of e.g. isoelectric focusing and the separated proteins can be transferred in a further station by means of connecting this transverse penetration with the separation channels. The type of separation is similar to the one of 2D electrophoresis.

In a further embodiment, the channels of the sample plates are formed at the edges such that the cross section of the penetration close to the openings is slightly reduced in Z-direction, to increase the adhesion of the separation matrix in the channel.

In a further embodiment, staining and de-staining is respectively carried out in separated chambers.

In further embodiments, further stations are conceivable for additional procedures:

drying of the gel alternative detection methods, e.g. radioactive detectors, UV-sources and detectors, laser or scanner, the wave lengths of which are not compatible with the common glass types chemical biological reactions prior to evaluation and prior to blotting, respectively.

It should be emphasized that the specifications for the directions are only to be understood exemplary and for an easier understanding. The actual orientation of the analysis and sample plates as well as additional means and also the order of the stations are arbitrary.

The term glass plate only is meant as an example. As material for the sample plates, all materials are considered which have a sufficient rigidity and flatness and are resistant against the chemicals used. The optical translucence is not necessary, if the optical detection is omitted during the other process steps. To be considered are, amongst others, glass, ceramics, sapphire, silicon, poly acryl amide, polystyrene, polyester, polyimide, polyurethane, polycarbonate, polyurethane, polyamide, polyethylene imines, polyarylen sulfide, polysiloxane, polyacetat, polysulfide and other plastics.

The material for the analysis plates additionally has to have high abrasion resistance and good thermal conduction. The above listed materials do qualify here also, but also locally optimized materials as e.g. glued plates for better heat conduction can be considered. The analysis plates typically have a thickness of 0.5-3 mm, which are enforced on the side facing away from the sample plate by sandwich-like additional plates, at least in the areas in which no peripheral means are attached.

In the following, the invention is described by means of further embodiments which are explained in detail with the drawings.

FIG. 1 The first embodiment I is a device according to the invention in side view. A separation chamber is integrated into a support structure.

Figure 2:
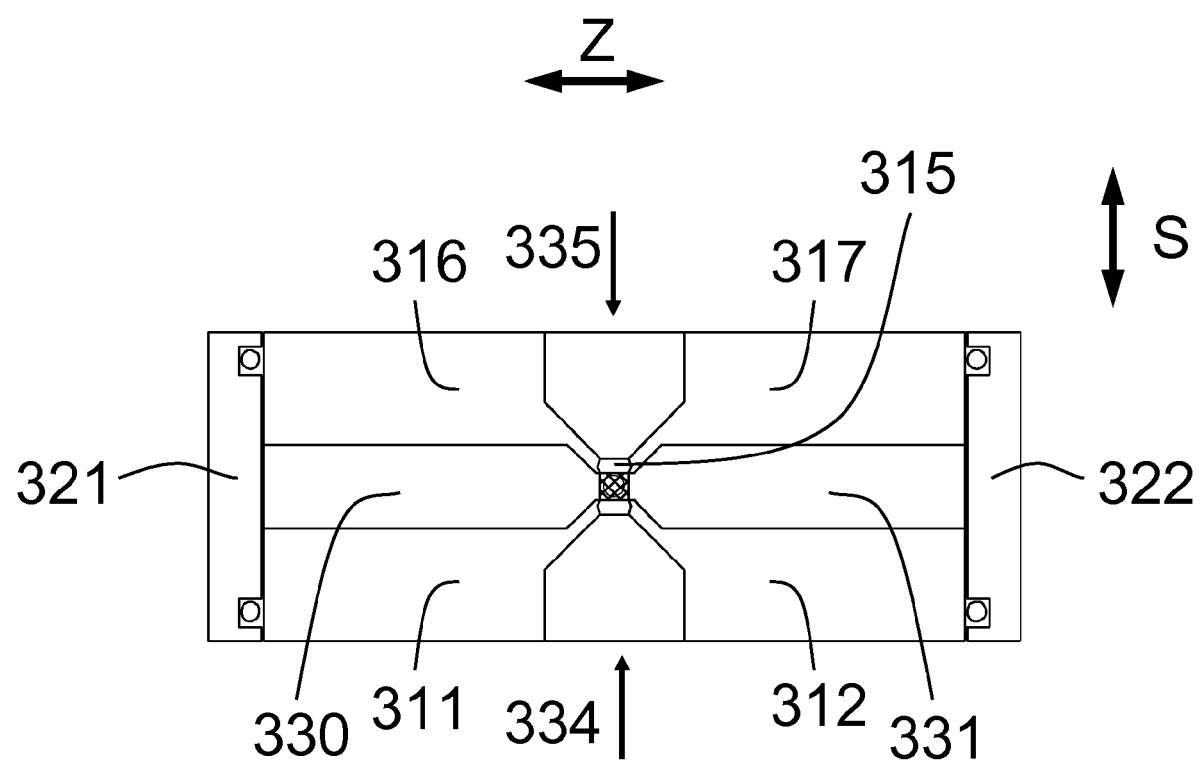

FIG. 2 The device according to FIG. 1 in top view.

Figure 3:
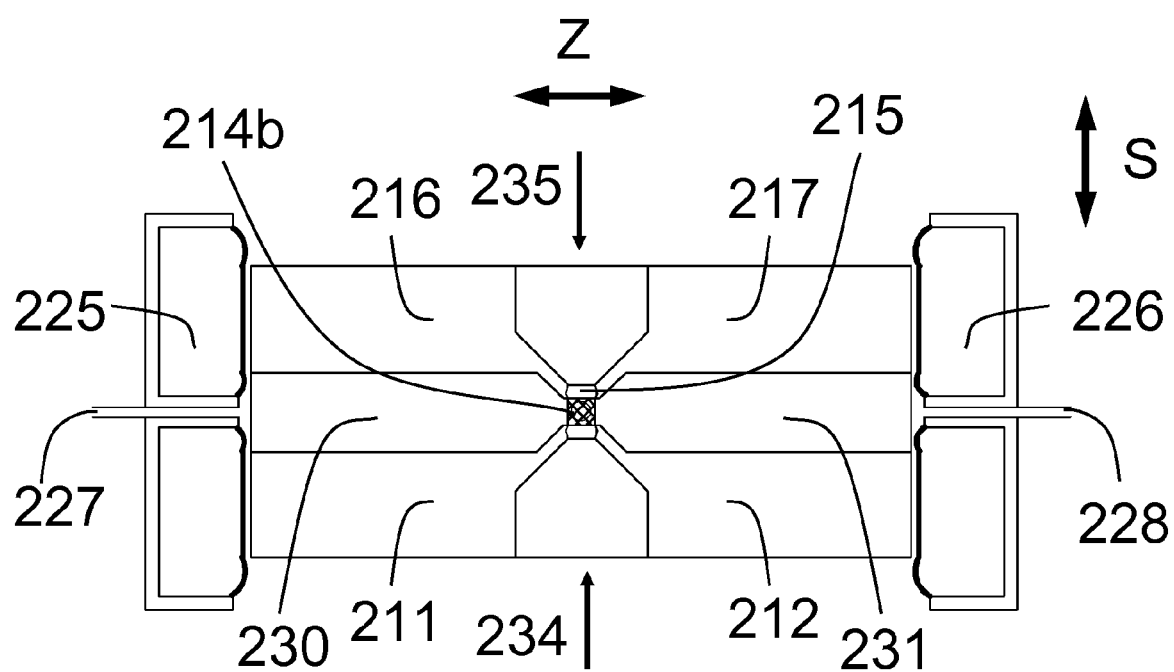

FIG. 3 A further embodiment II and III, respectively, of a device according to the invention in top view.

Figure 4:
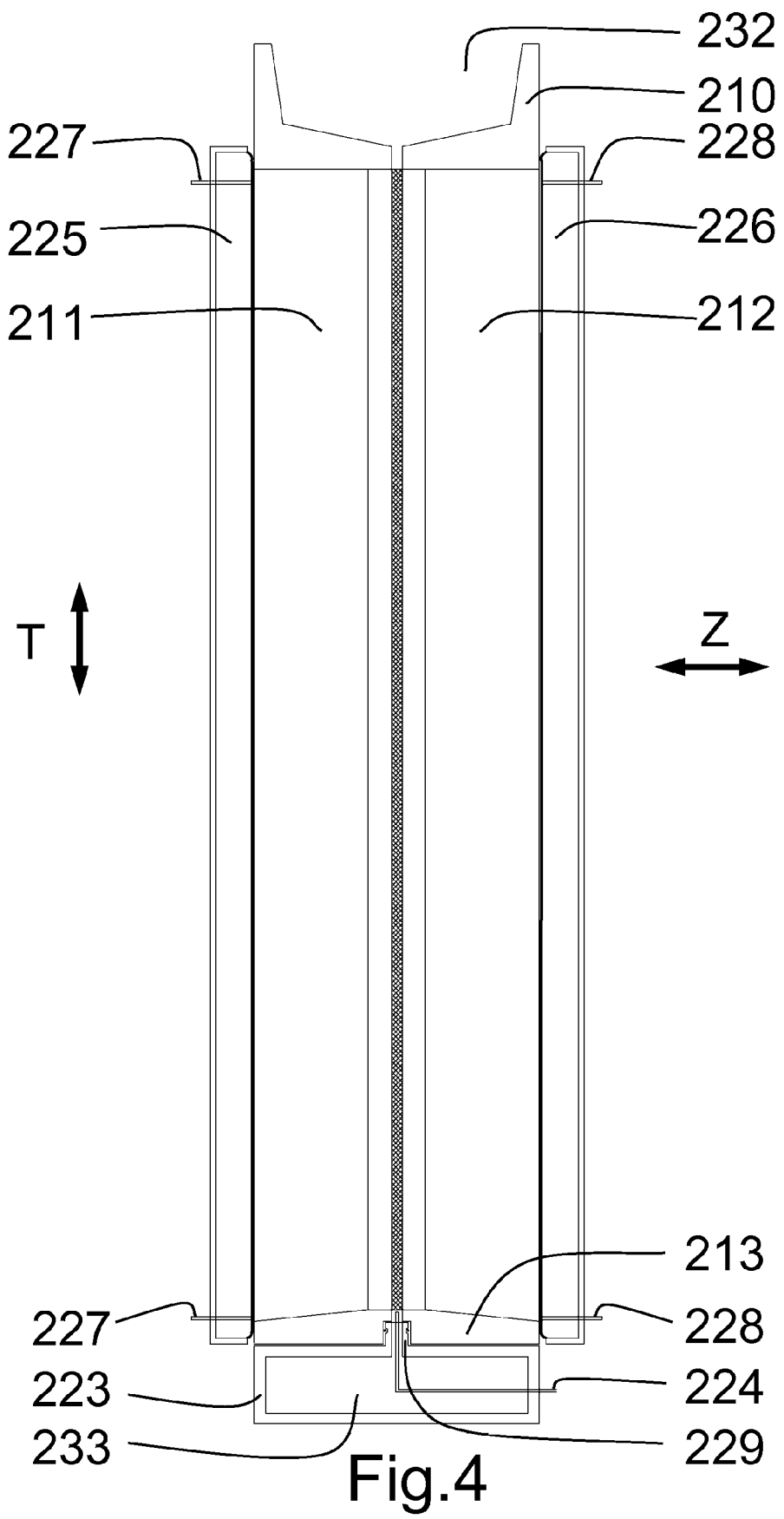

FIG. 4 The device according to FIG. 3 in side view.

Figure 5:
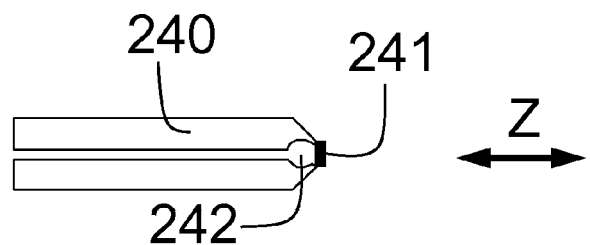

FIG. 5 The blotting plunger according to FIG. 3 in top view.

Figure 6:
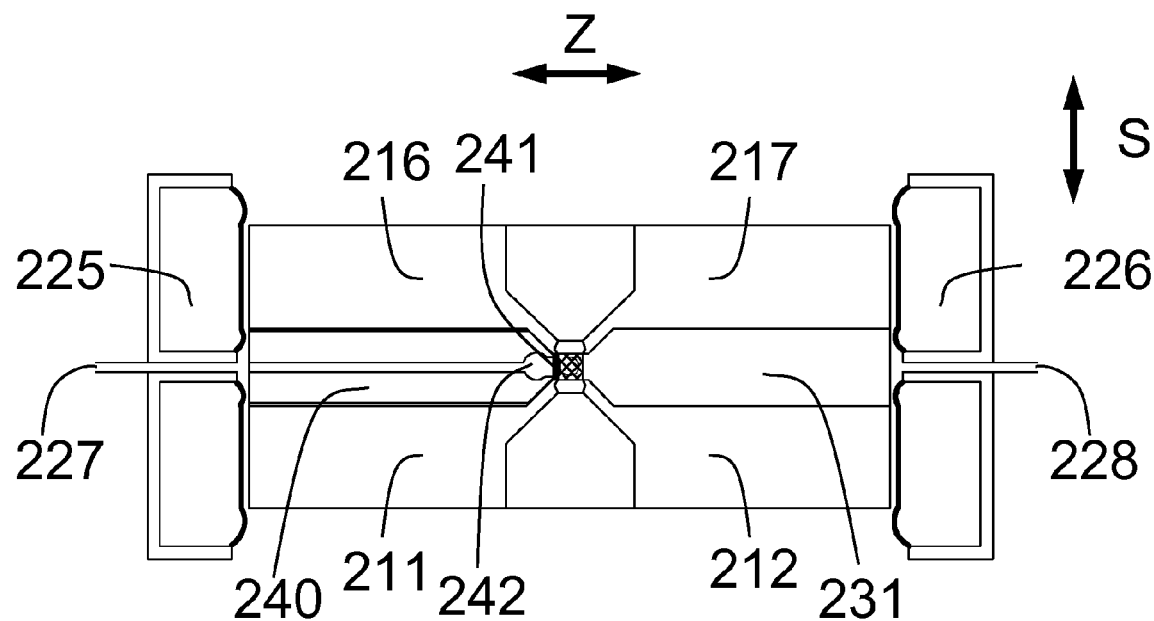

FIG. 6 The device according to FIG. 3 with the blotting plunger being inserted according to FIG. 5 in top view.

Figure 7:
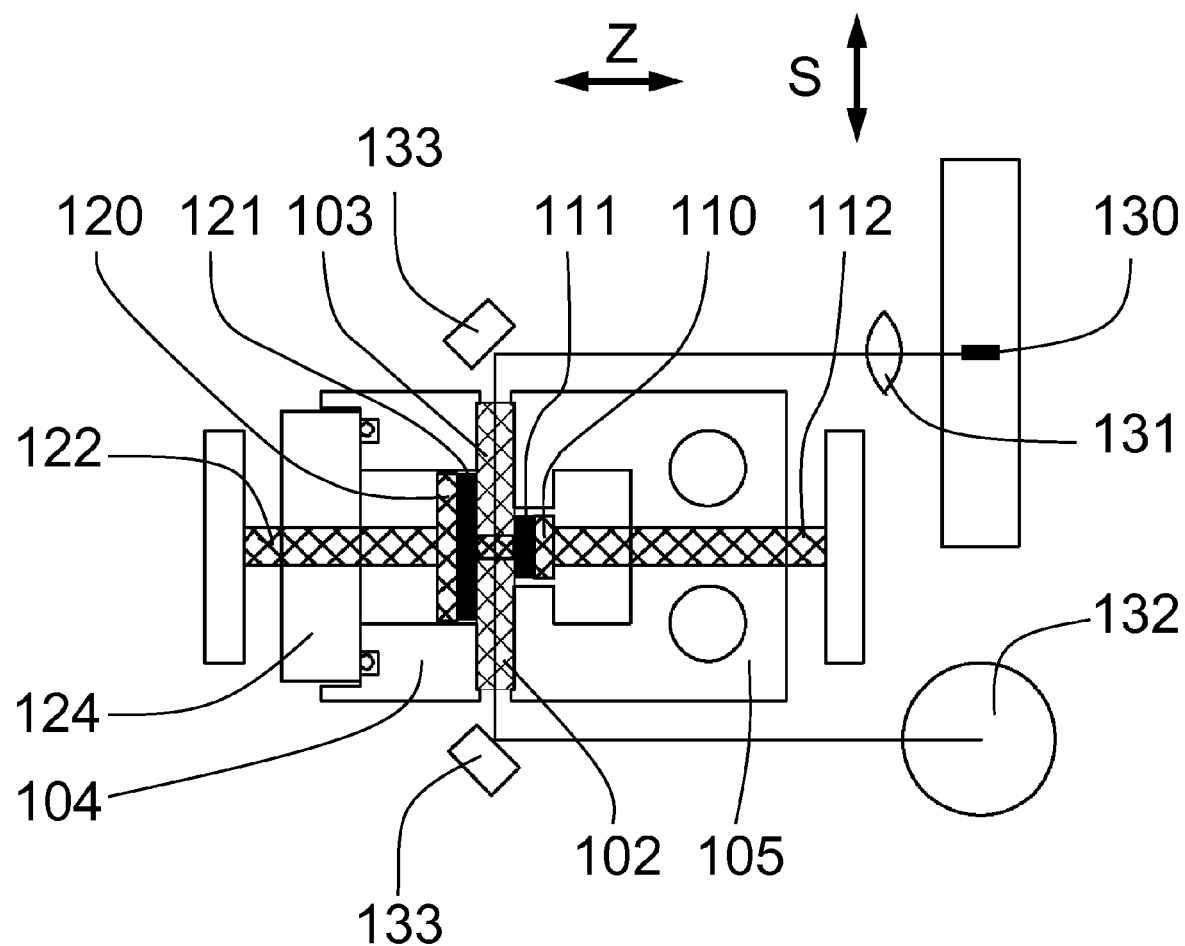

FIG. 7 A further embodiment IV of the device according to the invention in top view.

Figure 8:
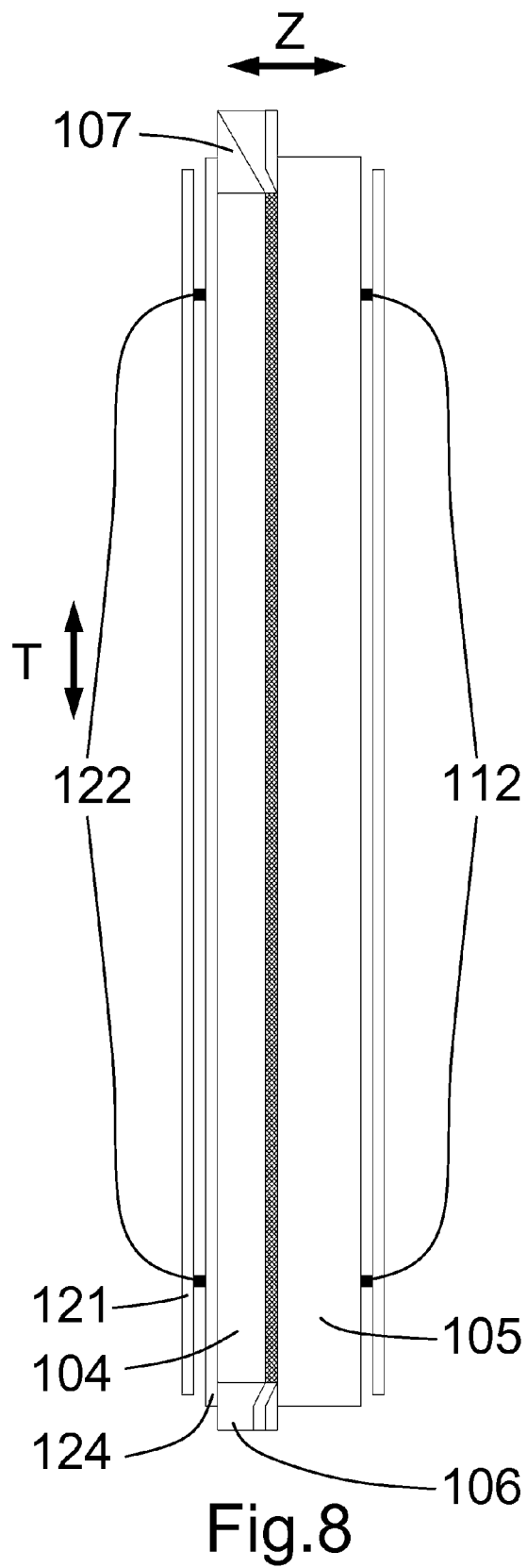

FIG. 8 The device according to FIG. 7 in side view.

Figure 9:
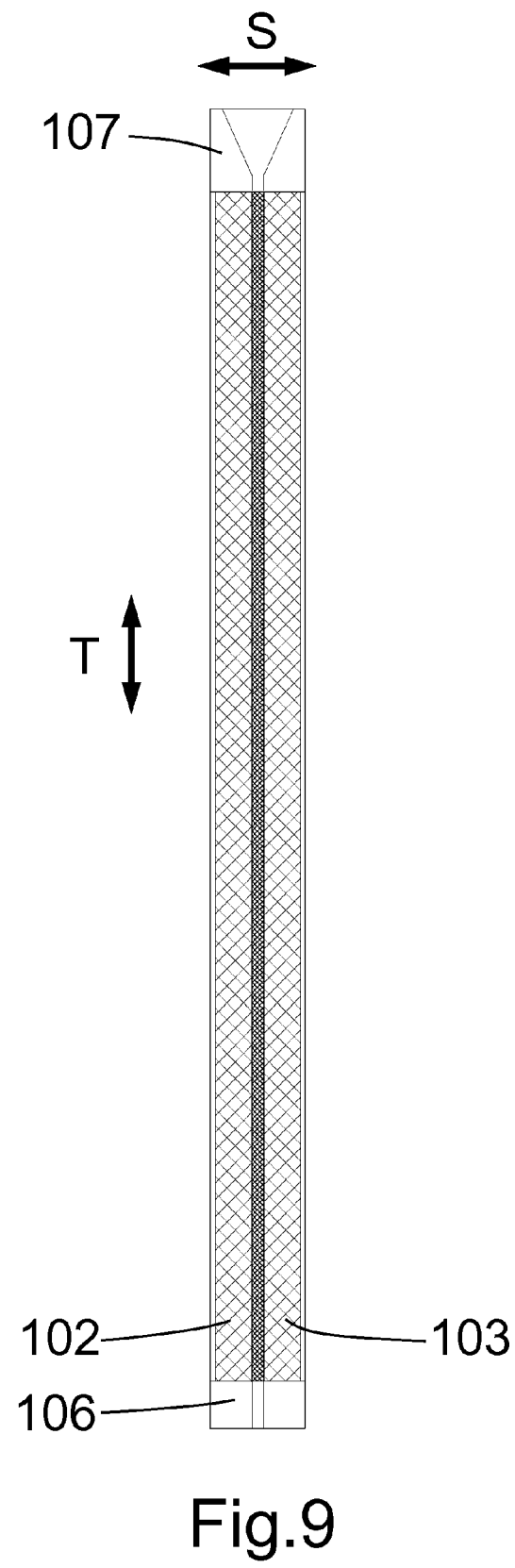

FIG. 9 The device according to FIG. 7 in front view.

Figure 10:
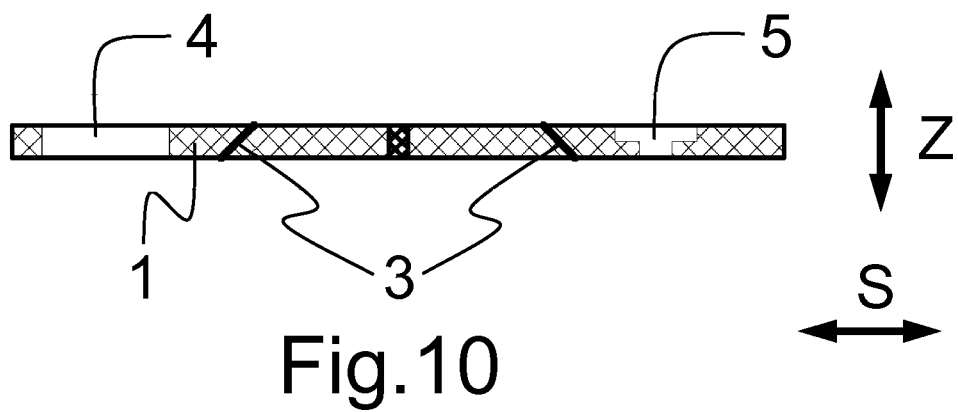

FIG. 10 A further embodiment V of a device according to the invention, constituted of a sample plate in top view.

Figure 11:
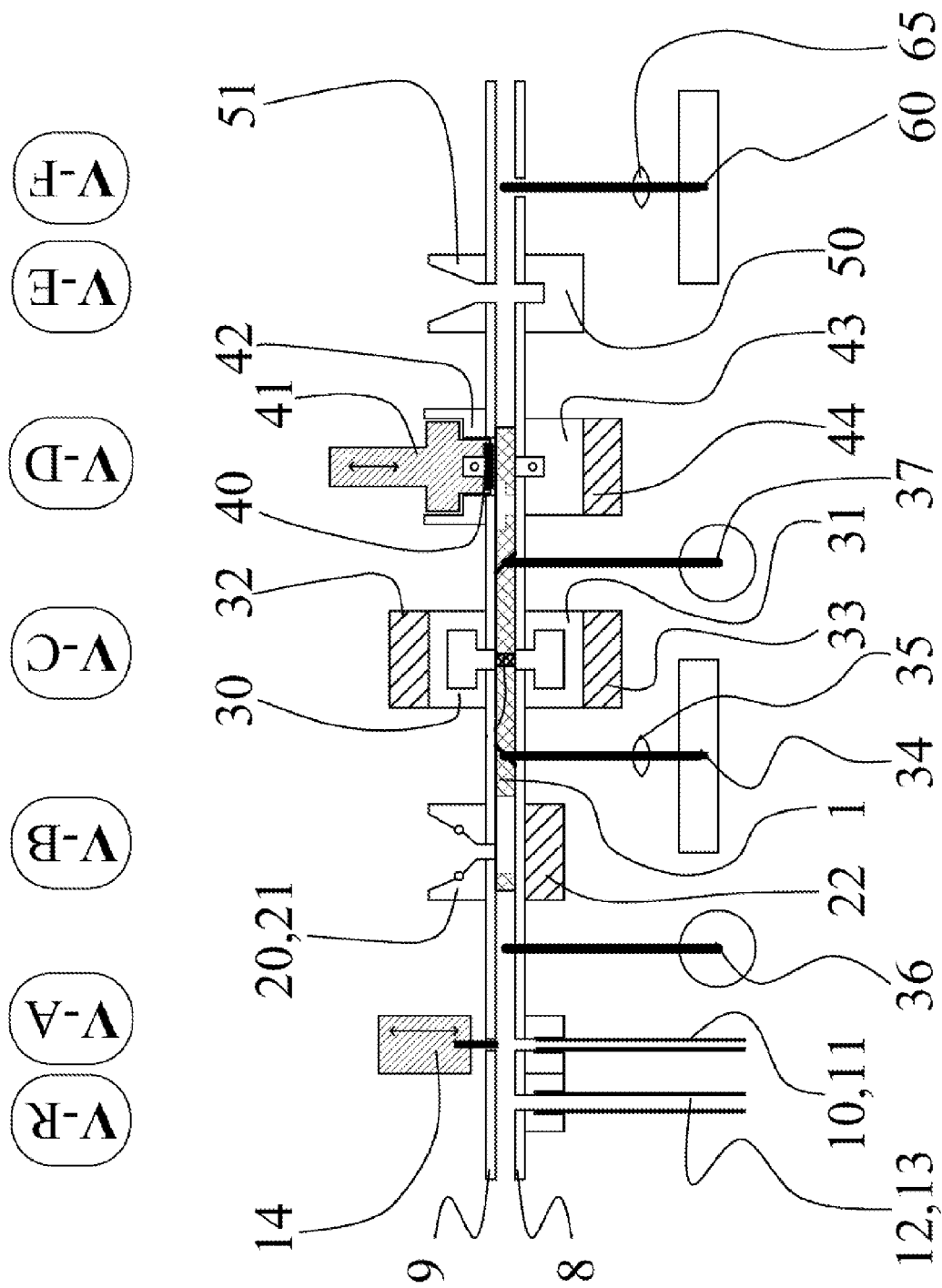

FIG. 11 The sample plate according to FIG. 10 between the associated analysis plates with associated stations.

Figures 12, 13:
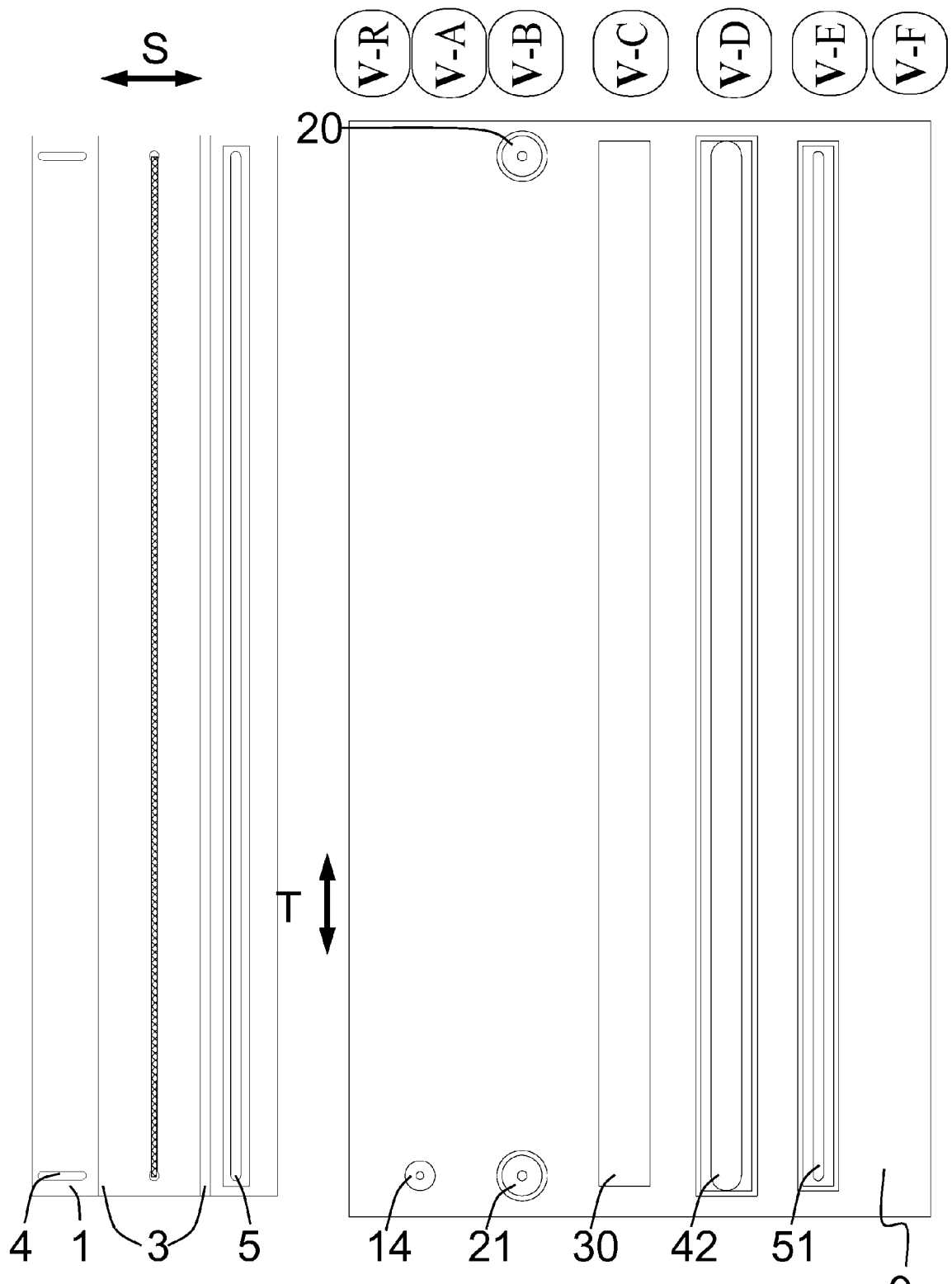

FIG. 12 The sample plate according to FIG. 10 in top view.

FIG. 13 The upper analysis plate according to FIG. 11 in top view.

Figure 14:
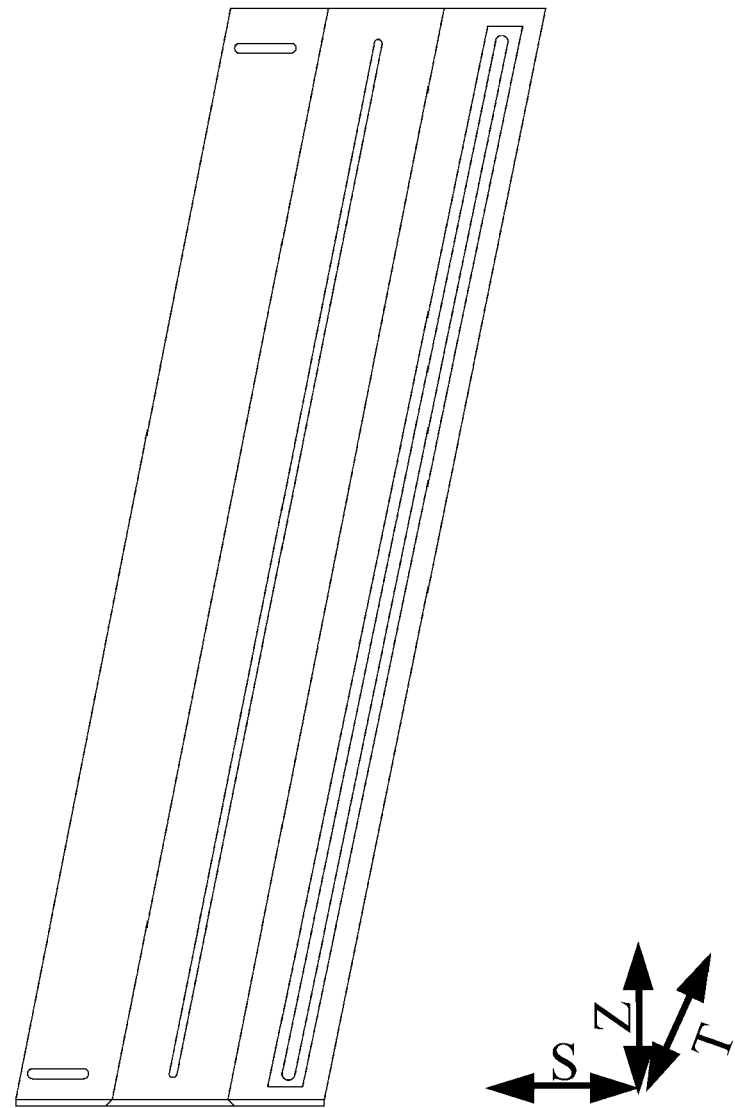

FIG. 14 The sample plate according to FIG. 10 in spatial illustration.

Figure 15:
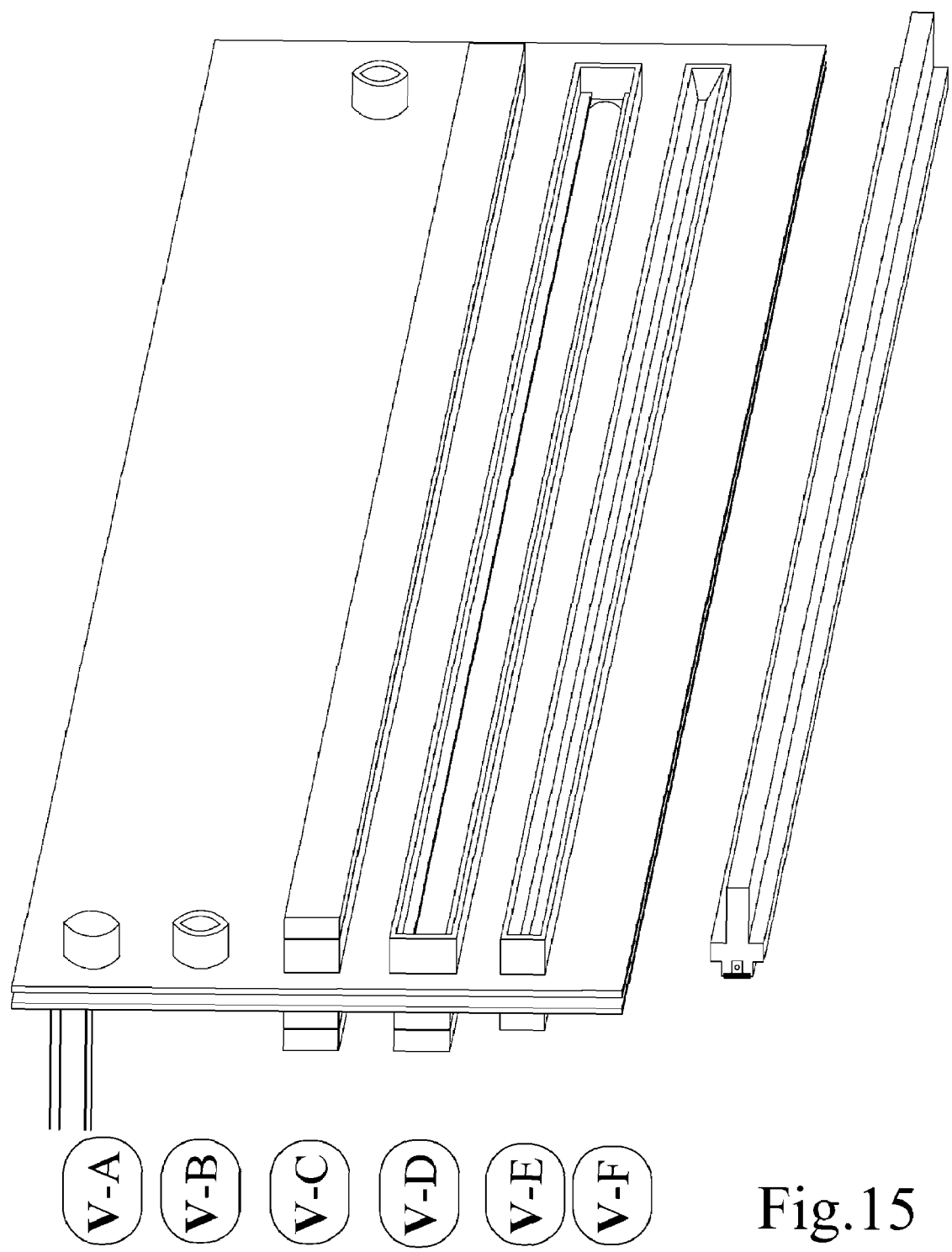

FIG. 15 The analysis plates according to FIG. 11 in spatial illustration with membrane plunger.

FIGS. 16a-e Detailed drawings of the analysis plates according to FIG. 11.

Figure 17:
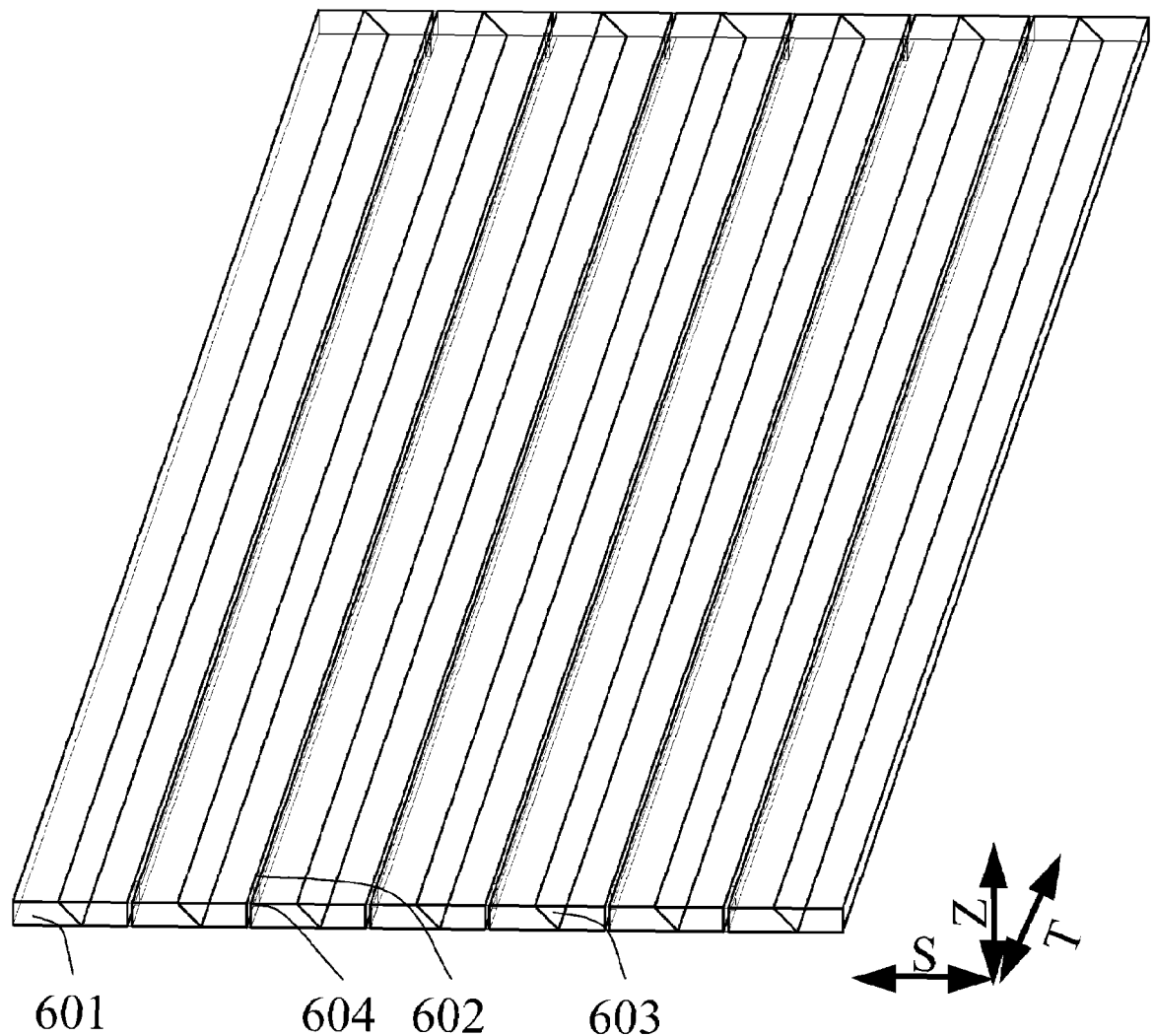

FIG. 17 A further embodiment VI of a device according to the invention, constituted of a sample plate in spatial illustration.

Figure 18:
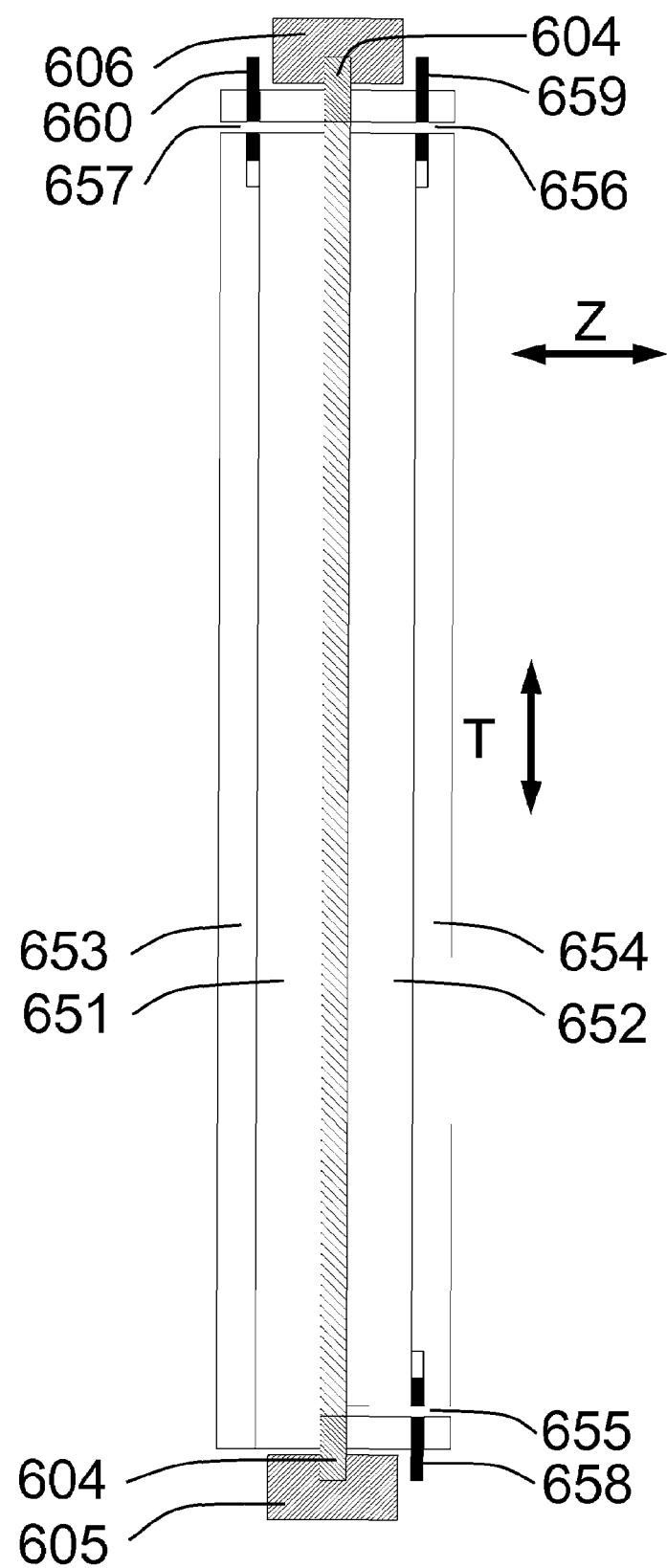

FIG. 18 The sample plate with pouring plates according to FIG. 17 in side view.

Figure 19:
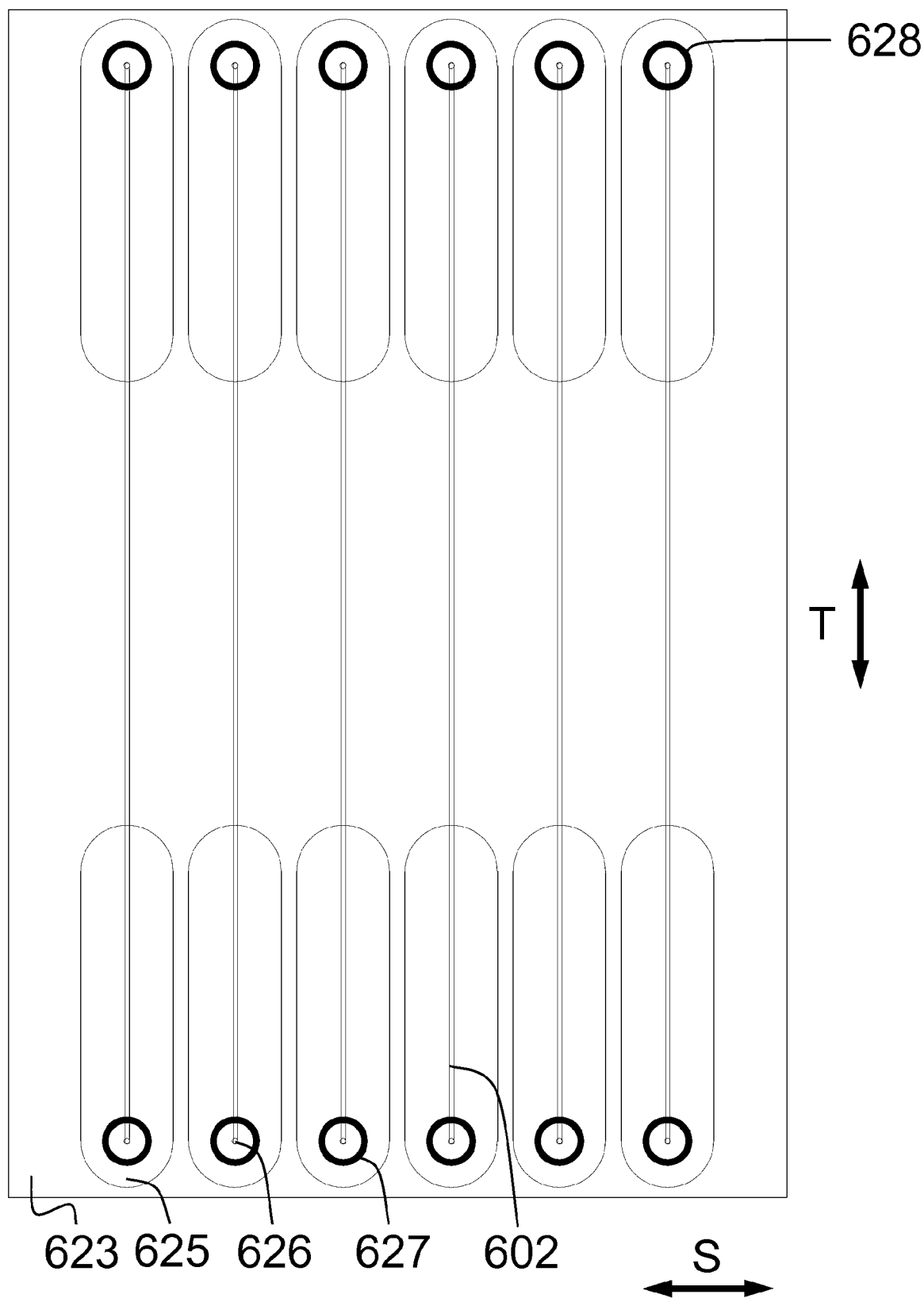

FIG. 19 The upper analysis plate according to FIG. 17 in top view.

FIG. 20 The sample plate with the analysis plates in separated position according to FIG. 17 in side view.

FIG. 21 The sample plate with the analysis plates in staining position according to FIG. 17 in side view.

FIG. 22 The sample plate and a membrane plate with the analysis plates in blotting position according to FIG. 17 in side view.

FIG. 23 The membrane plate with the analysis plates in reaction position according to FIG. 17 in side view.

FIG. 24 The membrane plate with the analysis plates in washing position according to FIG. 17 in side view.

FIG. 25 The membrane plate with the analysis plates in detection position according to FIG. 17 in side view.

Single Element Embodiment I

A gel channel 314 (in FIG. 1 in top view and in FIG. 2 in side view), having a rectangular cross section of typically 1×0.5 mm and a length of typically 100 mm, is enclosed from two opposing sides of 2 plates 315 being just as wide. The plates, preferably from glass or similar material, have a typical thickness of 0.05-0.5 mm and are optically completely translucent.

This gel channel is integrated with the glass plates into a plastic carrier, to close the different inlets to the gel channel against each other and to stabilize the system mechanically. The carrier has in profile (FIG. 2) a shape similar to a butterfly with opened wings. The wings are 311, 312, 316, 317. Cavities 330 and 331 are defined by these wings, serving for receiving the staining and de-staining agents. The cavities have direct contact to the gel channel.

The cavities 330 and 331 in operation are closed by 2 plates 321 and 322 fluid tight, which, however, are not part of the carrier but rather of the rest of the apparatus. They are pressed via rubber rings against the wings of the carrier. The carrier is closed at its end by 2 plates 310, 313 and is sealed. Also the plates 321, 322 of the main apparatus seal against these plates 310, 313 of the carrier. By this, said cavities 330, 331, leading to the gel 314, are completely closed. Via connectors 327, 328, being embedded into the wall 321, 322 respectively from top side and from bottom, it is possible to pass liquid into the cavities and to drain them again. The bottom 313 is inclined outwards for this purpose to facilitate a complete draining.

From top side, the gel channel is contacted by means of the reservoir 332. In its inside during operation, the electrolysis buffer for the source side is contained. The container 332 is part of the carrier, and has a base running conically to the centre. The opening in the base communicates with the gel channel and serves for loading of the gel, also for adding of the measuring substance. Subsequently, the beaker is filled with buffer liquid. Thereby, it can be beneficial, to obviate by means of a possibly perforated plate (not shown), which prevents the direct access to the applied measurement substance, the rinsing of the latter during filling of the buffer. Also, a further narrowing of the cross section of the inlet can be useful. Alternatively, the loading procedure can result wet i.e., at first the buffer is filled and in a $2^{nd}$ step e.g. by means of a pipette, the measuring substance is brought into a dent.

From below, the gel channel is contacted by means of the chamber 333. Thereby, a closed vessel 323 is concerned, belonging to the main apparatus, and being connected with the base plate 313 of the carrier via a rubber ring. It also contains electrolysis buffer. During attaching of the carrier, the reservoir at first is not filled. During the subsequent filling, at first, due to gravity, an air bubble is built up in the little tube 329, which would prevent wetting of the gel. By means of the capillary 324, this air bubble is sucked off at the highest position or can escape, respectively. Possibly it can be beneficial to embed a lateral dent into the base plate 313, which lies higher than the gel channel, but is not filled, and from which air can be sucked in an optimal manner. In the two reservoirs 332 and 333, respectively, the electrode is accommodated, serving for power supply during the electrolysis.

In FIG. 1, two further inlets 334, 335 to the gel channel 314 are visible. The gel 314, here, is covered with two glass plates 315.

From both sides 334, 335, the optical evaluation is carried out. This can result in transmission, then on one side 334 a light source is present, and on the other side 335 a detector, or in reflection, then detector and light source are on the same side, e.g. 335. As detector, an arbitrary sensor element, responding to the characteristics, can be considered which indicate the position of the different proteins.

Single Element Embodiment II

In FIG. 3 and in FIG. 4, an alternative embodiment of the main apparatus is illustrated. The plates 321, 322 of the main apparatus here are replaced by the vats 225, 226. These vats also close the cavities 230 and 231 of the carrier. The advantage lies within the very simple and save method for providing the sealing. The vats are respectively closed by a rubber membrane which can be retracted into the vat by negative pressure, and can be pressed against the carrier by overpressure uniformly. A pump, if necessary, also two pumps for overpressure and negative pressure, are sufficient, to close the cavities simultaneously at all carriers in the main apparatus.

The respectively double arranged capillaries 227 and 228 communicate with the cavities 230 and 231, and allow for the supply of liquids at the top into the cavities, and their discharge at the bottom.

The vats 225, 226 can be cooled and heated (not shown) from the side opposing the carrier. For better heat coupling to the liquid in the cavities 230, 231, it is possible to respectively provide the liquid inlets 227 and 228 with a large surface, and to let them protrude (not shown) into the cavities.

Single Element Embodiment III

In case blotting shall be carried out with a carrier subsequent to electrophoresis, thus a plunger 240 (see FIG. 5) is necessary. The plunger has the same vertical extension as the carrier, and fits precisely into the chamber 230 of the carrier (FIG. 6). At the tip, it carries as active element a blot membrane 241, which approximately is as wide as the gel channel 214. The gel channel also is covered on one side over the entire length and width by the membrane. At the beginning of the electrolysis procedure, the plunger is loosely placed in the chamber 230, without the membrane contacting the gel channel. As the vertical electrolysis procedure is completed, the membrane 241 of the plunger is pressed against the gel channel 214 by inflating of the rubber membrane of the vat 225. Buffer liquid can be supplied via several channels in the plunger from the capillary 227 into the vertical channel 242 of the plunger. This liquid Vets the membrane 241 from backwards. Simultaneously, buffer liquid is introduced into the chamber 231.

By this, the gel channel can be wetted on both sides by buffer on the long side 214 at fitting membrane 241. In both vets, electrodes are accommodated (not shown), dipping into the buffer and by means of which the current for blotting can be applied.

The main apparatus according to embodiment III, the main apparatus I, II are substantially equal.

In the main apparatus, respectively, two pumps are accommodated, to generate overpressure and negative pressure in the vats 225, 226. Thereby, the cavities 230 and 231 are sealed, or the plunger is pressed in blotting mode.

A pump with reservoir is present, to fill the tank 233 simultaneously at all carriers. A valve enables the closure of the capillary 224.

A pump with reservoir enables the filling of the container 232.

For each staining and de-staining and developer solution, which can be filled into one of the two cavities 230 and 231, a pump with reservoir is present (all carriers commonly).

A central effluent container is provided.

A central computer controls all procedures, it is connected to a calculator via a network interface, from which the operator controls the main apparatus.

The vats 225, 226 can be tempered by means of a heating and a cooling element, whereby also the liquid in the cavity 230, 231 of the carrier adopts this temperature.

To each carrier is assigned:
a) a detector for the separated measuring substance after separation
b) a light source
c) a power source for separation
d) a power source for blotting
e) a detector for the following labeler.

The detectors can be provided with a calibration light source, the main light sources can be provided with a calibration detector.

The measuring procedures embodiment III, the measuring procedures I, II are substantially similar.

A) Electrolytic Protein Separation and Detection:
1) A carrier is plugged into the main apparatus, and is thereby connected to the lower electrolysis tank 233. According to the number of the measuring substances to be measured, the necessary number of further carriers is plugged in. The rubber membranes of vats 225, 226 and the plates 321, 322, respectively, thereby are not abutting yet.
2) A metal capillary is folded into each container 232.
3) The measuring substances are filled into the carriers by means of a pipette.
4) A defined amount of buffer solution is filled into the container 232 from a reservoir by means of the metal capillary.
5) The container 233 also is filled with buffer solution. Thereby, the air escapes from the capillary 224. Thereby, the gel is contacted.
6) The two rubber membranes of vats 225, 226 are inflated, and the two plates 321, 322, respectively, are fitted to the carrier. Thereby, the cavities 230, 231 are closed and can be filled.
7) A current in a predetermined amount is applied to the gel via the metal capillary and the electrode of the tank 233. Thereby, each carrier is assigned to an individual power source. The measuring substance now runs in the gel and separates itself according to the molecular weight. After completion of this process, the current is switched off.
8) Now, stain liquid is filled into the cavities 230, 231 from a further reservoir. It can also be heated from the back of the vats via the heating facilities, to accelerate the reaction. The staining reaction can be adjusted arbitrarily according to temperature and time. After completion of the staining procedure, the stain liquid is pumped into the effluent container.

9) Now, the de-staining liquid for the gel is filled in. Again, the reaction time and reaction temperature are arbitrary. Thereafter, the de-staining liquid is pumped into the effluent container.

After completion of the gel treatment, evaluation is carried out:

10) The light sources are switched on in front of the carriers. The detectors register the light transmitted depending on the running distance in the gel, and therefore the intensity profile as function of the molecular weight in the measuring substance.
11) The computer analyses the data, and transmits it to the operator panel.
12) The air is deflated from the two rubber membranes of the vats 225, 226.

End of the automatic phase:

13) The operator removes the carrier.

B) Electrolytic Protein Separation and Blotting:

14) The plunger 240 is introduced loosely into a carrier.
15) The carrier is plugged into the main apparatus, and thereby is connected to the lower electrolysis tank 233. According to the number of the measuring substances to be investigated, the number of further carriers provided with plungers necessary is plugged in. The rubber membranes of the vats 225, 226 thereby do not abut.
16) A metal capillary is folded into each container 232.
17) The measuring substances are filled into the carrier by means of a pipette.

Beginning of the automatic phase:

18) A defined amount of buffer solution is filled into container 232 from a reservoir by means of the metal capillary.
19) The container 233 also is filled with buffer solution. Thereby, the air escapes from the capillary 224. Thereby, the gel is contacted.
20) The rubber membrane of the vat 226 is inflated. By this, the chamber 231 is closed and can be filled up.
21) Current in a predetermined amount is applied to the gel via the metal capillary folded inwards and the electrode of the tank 233. Thereby, each carrier is assigned to an individual power source. The measuring substance now runs in the gel and separates itself according to the molecular weight. After completion of this procedure, the current is switched off.
22) The rubber membrane of the vat 225 is inflated. By this, the plunger 240 is pressed against the gel.
23) Buffer is passed to the cavities 231 and 242 via the canula 227, 228. Thereby, the gel is contacted, and the membrane is abutting.
24) Current in a predetermined amount and duration is applied via the electrodes into the vats 225, 226. Thereby, the measuring substance is blotted from the gel onto the membrane. Subsequently, the current is switched off.
25) The air is deflated from the two rubber membranes of the vats 225, 226.

End of the automatic phase:

26) The operator removes the carrier from the main apparatus, and takes out the plunger with the membrane for further processing.

Single Element Embodiment IV

FIG. 7, FIG. 8 and FIG. 9 show the cross sectional, the side and the front view of the single elements. A channel 101, being typically 100 mm in length, is concerned, which is installed in a main apparatus, and can be filled automatically with gel, polymerizing subsequently in the channel.

The channel is delimited in one direction by two glass plates 102, 103, having the same width as the gel, typically 1 mm. The distance of the two glass plates of typically 0.5 mm determines the thickness of the gel. In the direction facing away from gel, the glass plates are substantially longer whereby it is possible, to connect the chamber 105 on one side with the glass plates in a water tight manner. On the other side, the chamber 104 is connected water tight with the glass plates, the cover 124 of which can be removed. The channel 101 is enclosed on its entire length by the glass plates and the two chambers. At the upper and lower end, two penetrated end pieces 106 and 107 serve for the necessary impermeability (FIG. 8 and FIG. 9). By these, the gel channel is contactable from top side and from the bottom.

Within the chambers, the gel channel 101 can be covered directly at its sides by the components of the two chambers 104 and 105: the plate 110 with the sealing 111 closes the channel from the right side over the entire length. The plate 120 with the sealing 121 closes the channel from left side over the entire length. Both plates can be pressed outwardly and can be retracted. For this, two sealed rods 112 and 122, being connected to the plates, protrude from the chambers 105 and 104 respectively. The rods are respectively connected to a plate for stability reasons, which allows for pressing and retracting of the sealing.

The light is directed from the light source 132 via the two mirrors 133 to the sensor 130, mostly a CCD-array. Hereby, the gel 101 is within the optical path and can be read out.

Main Apparatus Embodiment IV

In the main apparatus of embodiment IV, one or several of the above mentioned single elements are accommodated. Each of these elements can be used for analysis of a further analyte; however, they are operated commonly. For this, at one position in the main apparatus, reservoirs for the components of the gel prior to polymerization are provided. From these, the reaction container can be filled by means of pumps, including the gel substances in the desired mixing ratio. This liquid is directed to the funnels 107 of the gel channels 101 by means of a tube system. Further, a tube system with valves is provided at the outlet opening 106 of the gel channels. It flows into an effluent container. Further, a tube system is provided, filling buffer from a reservoir into the funnel 107. Further, a tube system is provided, supplying the chamber 105 with staining and de-staining solution, and in operation rinsing the gel by pumping over. The tube system enables also the filling of blotting buffer into the chamber 105. Further, a tube system is provided, supplying blotting buffer to the chambers 104. Cooling and heating elements enable the thermal stabilization of all liquid circulations.

Pneumatic cylinders serve for the common movement of all sealings 110 and 120 to the gel channel, springs press the sealings back again.

For each single element, a high voltage source is provided in the main apparatus, being connected to electrodes, passing into the buffer containers 107 and 106. The voltage source can also be connected to the electrodes and the chambers 104 and 105. For reading out the sensor elements 130, evaluation electronics is provided. A computer control controls the working cycles.

Measuring Procedure Embodiment IV

A) Pouring of the Gel into the Gel Channel 101
27) The two sealings 111 and 121 are pressed against the glass plates 102 and 103 by actuation of the plungers 112 and 122. Thereby, the gel channel is closed. Water, acryl amid and cross linking agent is supplied into the channel from reservoirs by the end pieces 107 in a predetermined concentration. The air is repressed in that an access amount liquid is discharged through the end piece.
28) The liquid in the capillary remains and polymerizes.
29) The two sealings 111 and 121 are removed from the gel channel.

B) Loading of the Analyte
30) The gel is loaded with the analyte via the end piece 107.

C) Electrophoresis
31) Buffer is filled into the end piece 107 via a capillary.
32) The end piece 106 being filled with gel is contacted by lifting the buffer mirror in a vat around the end piece. Thereby, both ends protrude into the electrically contacted buffer solutions.
33) Voltage is applied to the buffer solutions, the electrophoresis takes place.
34) During the electrophoresis, water of appropriate temperature is supplied in the chamber 105 through of cooling borings. Thereby, the desired temperature is adjusted in the gel.
35) The sensor 130 detects the running front of the gel.
36) At the end of the electrolysis, the voltage is turned off.

D) Staining
37) Staining solution is supplied from the reservoirs into the chamber 105.
38) During the staining, water of appropriate temperature is supplied into the chamber 105 through cooling borings. Thereby, the desired temperature is adjusted in the gel.
39) After completion of the staining procedure, residuals of the staining liquid are removed by means of water.
40) The separation matrix is cleaned with de-staining solution.
41) After completion of the de-staining procedure, residuals of de-staining liquid are removed by means of water.

E) Optical Evaluation
42) The gel is measured optically by means of a sensor, and the data is transmitted to the control computer.

F) Blotting
43) The cover 124 is removed by the operator, the sealing 121 is replaced by a blotting membrane and the cover is installed again.
44) The blotting membrane is pressed against the gel in the position of the sealing 121.
45) The chambers 104 and 105 are filled with blotting buffer.
46) By means of two electrodes in the two chambers, the blotting voltage is applied to the sandwich.
47) During the blotting, water of appropriate temperature is supplied into the chamber 105 through cooling borings. Thereby, the desired temperature of the blotting buffer and of the gel is adjusted.
48) The blotting membrane is retracted in the position of the sealing 121.
49) The operator removes the blotting membrane together with the cover 124.

G) Cleaning
50) Both sealings 111 and 121 are pressed against the gel channel.
51) Pressurized water is supplied into the effluent container through the gel channel via the end piece 107.
52) The chambers 104 and 105 are rinsed with water.

Single Element Embodiment V

In the embodiment V, the single element runs through different stations A-F, in which respectively one or more process steps are carried out. The gel channel is transported from a plate—the sample plate—to the single stations. In FIG. 10, FIG. 12 and FIG. 14, this plate 1 is illustrated in cross section in top view and diagonal from top. Typical dimensions are slightly more than 100 mm length and 1 mm thickness. A slot 2 in the middle, typically of 0.5 mm width and 100 mm length, receives the gel in operation. The edges of the slots are precise and sharp edged, to guarantee that the polymerized gel can be cut during displacement. In the plate, two optically reflective faces 3 are embedded at an angle of 45°. A possibility for their manufacture is: the plate with the integrated slot is cut at the corresponding position under 45°, is polished and metallizationed. Thereafter, the two parts are connected again. The possibility for manufacture of the slot is the assembling of the plate from two single plates, being held at a distance by means of a spacer at the ends. Further, slots 4 serve for cleaning and a vat 5 for receiving of a membrane.

In FIG. 11, the lower 8 and upper 9 analysis plates are illustrated together with the peripheral equipment necessary for each station in cross section. In FIG. 13 the upper analysis plate 9 is illustrated in top view. The sample plate 1 is enclosed from both analysis plates. FIG. 15 shows a spatial illustration of the analysis plates.

Mechanically, pneumatically or electrically it is ensured for the analysis plates to be pressed as tightly as possible against the sample plate 1 during the conducting of a procedure, that the channels of the sample plate are closed in a water tight manner unless corresponding penetrations are provided in the analysis plates. The displacement of the sample plate with the gel between the analysis plates for changing of the procedures becomes possible by releasing this mechanism.

In Station A gel is poured. An inlet 10 is provided from the bottom, contacting the channel 2. Also an outlet 11 is embedded from the bottom into the analysis plate 8 at the other end of the channel. A cylinder at the front side of the plunger 14 can also be pressed through the analysis plate 9 in the channel 2 of the sample plate. The channel comprises at this position a preferentially circular extension of the diameter of this cylinder. In rest position, a spring holds the plunger above the analysis plate. The two outlets 12 and 13 having an increased cross section, are assigned to the station R, serving for the cleaning of the in- and outlets 10, 11. The two penetrations 4 of the sample plate correspond thereto.

In station B, the sample substance is applied to the separation matrix and is separated. Two funnels 20 and 21 are connected by means of penetrations in the upper analysis plate to the ends of the channels 2. They contain electrodes for contacting a liquid filled thereto. The gel channel communicates with a heat exchanger 22 by means of the lower analysis plate, comprising the entire length of the channel. The heat exchanger can be realized e.g. as Peltier-element or as metal channel penetrated longitudinally, which can be rinsed with liquid. Such a heat exchanger can also be arranged on the upper analysis plate between the two funnels (not shown).

Further, in station B, the optical detector 34 can be positioned, to detect the running front. The optical path of the light runs from the light source 36 via a mirror 3 integrated into the sample plate 1 through the gel channel 2, via lens 35 into the detector 34. (In FIG. 11, the sample plate is shown in station C, the optical path emanates in this position from the alternative light source 37).

In Station C, gel is stained and read out. Two sealed chambers 30 and 31 are connected to the gel channel 2 by means of penetrations in the upper and lower analysis plate. The chambers can be brought to an adequate temperature by heat exchangers 32 and 33. Further, in station C the optical detector 34 can be inserted.

The optical path of the light runs from the light source 37 via the mirror 3 integrated into the sample plate 1 through the gel channel 2 via the lens 35 into the detector 34.

In station D (see FIGS. 11, 16a, 16b), the gel is blotted. The chamber 43 with an integrated electrode contacts the gel channel 2 by means of a penetration in the lower analysis plate. The chamber can be brought to an adequate temperature by means of a heat exchanger 44. The chamber can be brought to a slight overpressure by the inlet, to accelerate the blotting procedure. The gel channel is contacted from top side through a penetration in the upper analysis plate, being confined by a vat 42 being open at the top. In the vat, a plunger 41 can be inserted which is provided with a membrane 40 at the front side, which rests directly on the gel channel 2 through the relatively wide penetration. At the back of the membrane, a cavity is provided, comprising an electrode. The cavity can be filled with liquid, and a negative pressure can be generated therein. A spring holds the plunger in rest position above the channel.

In Station D (see FIG. 16c), a second position D1 of the sample plate is possible, in which the membrane can be deposited in the dent 5 of the sample plate. This is supported by a slight overpressure in the cavity of the plunger 41.

In station E (see FIG. 16d), an immune reaction is carried out at a membrane 40 lying in the dent 5 of the sample plate 1. For this, an immune reagent is filled from the top into the vat 51, and in the chamber 50 a slight negative pressure is generated from the bottom.

In station F (see FIG. 16e) the membrane strip is read out by means of the sensor 60 with the lens 61.

In a further station, the gel channel is brought into contact with a 2D gel. The arrangement is not illustrated explicitly. It corresponds to station D, with the difference that instead of the blotting plunger 41, a gel channel with two plates and enclosed gel is employed. Typical dimensions of the gel chamber are: 100 mm length (as the gel chamber 2), 0.5 mm thickness of the gel, and 50-100 mm running length of the gel away from the upper analysis plate.

Main Apparatus Embodiment V

In this main apparatus of embodiment V, one ore more of the above mentioned single elements are accommodated. Each of the elements can be used for analysis of a separate analyte, but however is operated together with further elements. For this, many sample plates are coupled horizontally in the main apparatus mechanically, preferentially such that the gel channels are parallel. Thus, they can be moved commonly by means of the displacement mechanism. The easiest way to carry this out is by means of a continuous glass plate. Also, the single analysis plates are respectively coupled to the common continuous plate. Thereby, a very simple mechanism is enabled which can bring a number of gel channels commonly in the respective positions. An alternative construction is the use of single glass plates, constituting the complete sample plate. These glass plates are held on both longitudinal sides by two guiding devices, ensuring the correct spacing between the glass plates and enabling the common movement.

The heat contact to the gel channel can also be guaranteed even under omitting all of the heat exchangers described in the single construction in that the entire lower analysis plate lies in a vat filled with liquid. Sensor elements 34, 35 and light sources 36, 37 have to be attached to the vat externally in this case. If no liquid-free accesses are provided, the optical path additionally runs through the cooling liquid.

The upper analysis plate is attached foldably, to enable a very simple maintenance of the sample plate. A further plate is attached above the upper analysis plate also foldably. It carries the supply capillaries to the funnels of the upper analysis plate, the mechanism for pressing the upper analysis plate, the mechanism for pushing the sample well plunger, and the mechanism for pushing the blotting plunger as well as the electrode supplies.

In the main apparatus, the reservoirs for the components of the gel prior to polymerization are provided. From this, a reaction container can be filled by means of pumps, including the gel substances in the desired mixture ratio. From this, the capillary 10 is filled by means of a tube system and valves. Further, a tube system with valves is provided at the outlet capillary 11 of the gel channels. It flows into an effluent container. Further, a tube system is provided, filling buffer into the funnels 20 and 21 from a reservoir. Further, a tube system is provided, supplying staining and de-staining solution to the chambers 30 and 31, and in operation, rinsing the gel by pumping over. Further, a tube system is provided, supplying blotting buffer to the chambers 43 and 42.

For each single element, a high voltage source is provided in the main apparatus, which can be connected to the electrodes in the funnels 20 and 21. The voltage source can also be connected to the electrodes in chambers 42 and 43. For reading out the sensor elements 34, evaluation electronics are provided. A computer control controls the working steps.

Measuring Procedure Embodiment V

Station A) Production of the Separation Matrix
- 53) The upper analysis plate 9 is loosened, the sample plate 1 is brought into position A and the upper analysis plate 9 is pressed on again.
- 54) The sample well plunger 14 is pressed inwards by the pneumatics.
- 55) Buffer solution, acryl amid, and cross linking agent in a predetermined concentration is collected in a mixing chamber from the reservoirs, and is supplied through the capillaries 10 into the gel channel 2. The air is repressed in that an excess amount of liquid is discharged through the capillary 11.
- 56) The liquid in the gel channel 2 remains there and polymerizes.
- 57) The sample well plunger 14 is released.

Station B) Loading of the Analyte and Separation
- 58) The upper analysis plate 9 is loosened, the sample plate 1 is brought into position B, and the upper analysis plate 9 is pressed on again.

59) The gel is loaded by the operator via the funnel 20 with the analyte.
60) Buffer is filled into the funnel 20 and 21 via one respective capillary.
61) A voltage is applied to the buffer solution via the electrodes, electrophoresis takes place.
62) The heat exchanger and the vat under the lower analysis plate, respectively, provide for the desired temperature of the gel.
63) The sensor 34 detects the running front of the gel.
64) The voltage is turned off when electrophoresis is completed.

Station C) Staining and Optical Evaluation

65) The upper analysis plate 9 is loosened, the sample plate 1 is brought into position C and the upper analysis plate 9 is pressed on again.
66) Staining solution is supplied into the chambers 30 and 31 from the reservoirs.
67) The heat exchanger and the vat under the lower sample plate, respectively, provide for the desired temperature of the gel.
68) After completion of the staining procedure, the staining liquid is drained, and de-staining solution for de-staining of the separation matrix is supplied into the chambers 30 and 31 from the reservoirs.
69) After completion of the de-staining procedure, the de-staining liquid is drained.
70) The gel is optically measured by means of the sensor, and the data is transmitted to the control computer.

Station D) Blotting the Analyte on a Membrane

71) At the beginning, simultaneously with the loading of the analyte, the blotting plunger 41 is provided with a blotting membrane.
72) The upper analysis plate 9 is loosened, the sample plate 1 is brought into position D, and the upper analysis plate 9 is pressed on again.
73) The chamber 43 and the cavity of the plunger 41 are filled with blotting buffer.
74) The blotting plunger 41 is pressed on by pneumatics.
75) A voltage is applied to the buffer solutions via the electrodes, the blotting takes place. This procedure can be further intensified by negative pressure and overpressure, respectively, and can result exclusively thereby.
76) The heat exchangers and the vat under the lower analysis plate, respectively, provide for the desired temperature of the gel.
77) The blotting plunger 41 can be removed by the operator, or remains within the apparatus, to carry out the immune detection.

Station E, F) Immune Detection on the Membrane

78) The blotting plunger 41 is retracted by the spring.
79) The upper analysis plate 9 is loosened, the sample plate 1 is brought into position D1, and the upper analysis plate 9 is pressed on again.
80) The blotting plunger 41 is pressed on by the pneumatics.
81) A slight overpressure is generated in the cavity of the plunger 41. The membrane 40 thereby is pressed into the cavity 5 of the sample plate 1.
82) The blotting plunger 41 is retracted by the spring.
83) The upper analysis plate 9 is loosened, the sample plate 1 is brought into position E, and the upper analysis plate 9 is pressed on again.
84) The immune reagent is filled into the vat 51, and is drawn by a slight negative pressure into the chamber 50 through the membrane.
85) Now, washing steps can be carried out on the membrane, which can e.g. be carried out in station C. Further subsequent immune reagents can be applied in station E.
86) The upper analysis plate 9 is loosened, the sample plate 1 is brought into position F, the upper analysis plate 9 is pressed on again.
87) The proteins positioned on the membrane are detected by means of the detector 60 by luminescence or optical reflection or other methods.

Station R) Cleaning

88) The upper analysis plate 9 is loosened, the sample plate 1 is brought into position R, and the upper analysis plate 9 is pressed on again.
89) Water and subsequently diluted NaOH is rinsed under increased pressure through the channels 4 into the capillaries 12 and 13, and thus into the effluent container from the capillaries 10 and 11.
90) The upper analysis plate 9 is loosened, the sample plate 1 is brought into position A, and the upper analysis plate 9 is pressed on again.
91) Pressurized water is rinsed through the gel channel 2 into capillary 11, and thus into the effluent container from the capillary 10.

Pouring, Analysis and Immune Section of Embodiment VI

In the embodiment VI, several single gel channels are accommodated in a sample plate, preferentially parallel. FIG. 17 shows such a plate 601, including six channels in the example shown. Typical dimensions of the plate are 1-2 mm thickness (Z-direction), 50-100 mm length (T-direction), and 5-10 mm distance between two channels (S-direction). The total width results from the number of channels. The width of a gel channel 602 typically is 0.1-1 mm. The plate is comprised of glass or plastic strips, which are held in an adequate distance by spacer 604. The channel side faces have an optically faultless surface. Each of the glass strips comprises a mirror 603, which is embedded into the strip such that light can be deflected from both Z-directions in S-direction. Mostly, an angle of 45° will be appropriate for this. The parts of the sample plate are connected to each other fixedly, preferentially by gluing with optically adequate cement, and are reinforced at the edge by the holders 605 and 606, shown in FIG. 18.

According to the embodiment VI, the generation of the gel matrix (pouring) and the actual analysis takes place in separated areas of the same main apparatus. This enables the removal of the sample plates between gel manufacturing and gel application, the supply inventory of gel plates, and increases the throughput of the apparatus, because a gel can cure in the pouring section in a sample plate, and an analysis can be carried out with a second sample plate parallel. The cleaning of the used plates is also carried out in the pouring area.

The pouring area is illustrated in FIG. 18 in longitudinal section through the gel channel. The sample plate 601 with the holders 605 and 606 is enclosed by the two pouring plates 651 and 652. In T-direction, the spacer 604 closes from top and bottom the gel channel 602. The inlets 655, 656 and 657 enable the filling of the gel channel. To be able to remove the sample plate prior to curing of the gel, sliders 658, 659, and 660, with which these can be closed, are provided at the inlets.

These sliders are pushed by the auxiliary plates 653 and 654 against the pouring plates 651 and 652, and seal in the inserted state.

In a further embodiment, inlets 656 and 657 are longitudinally enlarged in T-direction, to increase the height of the stacker gel.

FIG. 19 shows the separation station of the analysis area in top view, FIG. 20 in a side view. The upper analysis plate 623 is translucent, thus in FIG. 19 one can view the channels 602 in the sample plate 601 lying there underneath. The vats 625, which are cut into the plate 623, serve for receiving of the buffer solution. They flow into the sample wells 626 of the second layer 622 of the analysis plate lying there under. Therein, ring-shaped electrodes 627 are provided. At both ends of each gel channel, one respective complete vat construction is attached. The lower analysis plate 621 lies underneath the sample plate 601.

In FIG. 21, a staining station is shown. The lower analysis plate is composed of two layers 634 and 631. Thereupon, the sample plate 601 is provided. The upper analysis plate with the layers 632 and 633 presses onto the sample plate 601. In both analysis plates, a chamber 635, 636 is integrated, being connected with each of the gel channels 602 in Z-direction. From the light source 637, light is incident on the mirrors 603 in the sample plate in Z-direction, which these deflect in S-direction, passing it through the gel channels, and directing it again in S-direction out of the sample plate from the back side of the neighboring mirror. Further mirrors 638 reflect the light onto the detector 639. In the optical path, a lens, not shown, is provided. In the detector, slightly parallel displaced strips are generated, according to the images of the channels.

FIG. 22 shows a blotting station in side view. The upper analysis plate consists of two layers 642, 643. The lower analysis plate 641 has a section, in which the plunger 644 rests. It supports the membrane plate 610, which contains the membrane 649 in a dent. The plunger 644 can be lifted and lowered pneumatically, electrically or mechanically, whereby it is possible to push the membrane 649 against the sample plate 601. Thereby, there is a contact in Z-direction between the gel channel 602 and the membrane 649. If the sample plate is shifted to the side, the membrane plate can be pressed against the analysis plate 642. If the upper analysis plate 642 is lifted slightly, it is possible to displace the membrane plate laterally between the analysis plates. In the upper analysis plate 642, a chamber 645 is integrated in the plunger 644, a chamber 646 is integrated. The openings in the membrane plate 610 connect the chamber 646 with the bottom side of the membrane. The chambers contain the electrodes 647 and 648. Slight negative pressure in the chamber 646 fixes the membrane; slight overpressure pushes it against the sample plate.

For increasing the throughput and for facilitation of the apparatus, the immune reaction, the washing steps, and the detection are carried out in a separated apparatus part in the immune section. The membrane can be transported thereto automatically in that it is threaded in the slot between the analysis plates by means of the plunger 644. Also the manual transport is possible. This does not represent a substantial impairment of comfort, because the application of the immune reagents in general is carried out manually, to use the expensive reagents as efficiently as possible.

FIG. 23 shows the reaction station of the immune area in side view. The membrane plate 610 has a slight dent, in which the membrane 649 rests. The lower and upper analysis plates 671 and 672 seal the membrane plate. By means of the reagent wells 675 which expand in T-direction over the entire length of the matrix channel or only over a partial length, liquid can be applied onto the membrane plate in this area, in that during the blotting, the separated analyte is penetrated into the membrane. This can result manually as well as automatically.

In FIG. 24, a washing station is illustrated. A membrane plate 610 with the inserted membrane 649 is enclosed by the lower and upper analysis plates 681 and 682 and is sealed. The second layers 683, 684 of the upper and lower analysis plates enclose respectively a chamber 685 and 686 with the first layer. The chambers contact the membrane in the area in which the immune reaction has resulted from top and from bottom.

In FIG. 25, a detector station is shown. The membrane plate 610 with inserted membrane 649 is enclosed and sealed by the lower and upper sample plate 691 and 692. The membrane is illuminated in the area of the immune reaction through the translucent surface of the upper analysis plate 692 by means of light sources 697. The reflected light is directed by means of the mirror 698 onto the detector 699. There, slightly parallel displaced strips are generated, mapping the areas of immune reaction.

In a further embodiment VII, the stations R and W are integrated into station B. The $2^{nd}$ layer 643 of the upper analysis plate 642 can be folded upwards, to be able to fill immune reagents manually into the dents of the chamber 645 which are formed as reaction wells as in station R. The station D is replaced by a detector plate, being arranged instead of the sample plate 601, above the membrane plate. This can result in that the plunger terminates approximately with the lower analysis plate, or in that the plunger is driven downwards such far that between the lower analysis plate 641 and the plunger 644 sufficient space remains. As detector in the detector plate, an arrangement can be used as in station D, or a film, which is exposed on the membrane. The membrane plate can be integrated into the plunger.

In a further embodiment, all analysis and pouring plates for supporting the sealing effect at the contact faces with the sample plate and the membrane plate are provided with adequate sealings in two dimensional form or in lines.

Main Apparatus of the Embodiment VI

In the main apparatus, the pouring area, the analysis area, and the immune area are accommodated. According to the embodiment, the sample plate and the membrane plate are transported between the sub areas manually or automatically. Between the stations separating (T) FIG. 20, staining (F) FIG. 21, and blotting (B) FIG. 22 of the analysis area, the sample plate is moved by means of a stepping motor. The analysis plates of the single stations have a continuous surface for this purpose. For cleaning, they are foldable upwards. For each of the chambers, pipes, reservoirs, valves and pumps are available, to fill them with the necessary reagents and to discharge them. For each channel, a high voltage supply is available, which is connected with the corresponding electrode pairs. For cleaning of the analysis plates, terminals are provided through which the spacing, in which the sample plate can be displayed, can be flooded with water and diluted NaOH.

In the pouring area, there is a mixing chamber for generation of the gel. Tubes, pumps, valves, and reservoirs enable the filling and cleaning of the sample plate.

In the immune area the membrane plate with the inserted membrane is moved between the reaction station (R), the washing station (W), and the detector station (D) by means of a stepping motor. Cleaning terminals are provided. Also, pipes, pumps, valves and reservoirs are available here, to carry out the single operations.

For reading out of the sensor elements, evaluation electronics are provided. A computer control controls the working steps.

Measuring Procedure Embodiment VI

Pouring of the gel matrix:
92) In the pouring area, a sample plate 601 is inserted between gel plates 651 and 652, and all parts are pressed against each other (manually) by means of clamps.
93) In the mixing chamber, separation gel is produced from the stored reagents.
94) Gel is filled in excess into a channel 602 of the sample plate 601 through the inlet 655 by means of a pump from the mixing chamber. Thereby, at first air escapes through the inlet 656 and then gel in excess. The slider 660 is closed thereby.
95) The inlet 655 is closed by means of the slider 658, the slider 660 is opened.
96) In the mixing chamber, stacker gel is produced.
97) The stacker gel is filled into the upper section of the gel channel through the inlet 657, where it replaces the running gel on the width of the inlet.
98) The sliders 659 and 660 are closed.
99) The pipe system and the mixing chamber are rinsed with water.
100) The sample plate with gel can remain within the apparatus during the polymerization, or can be removed.
101) After completion of the polymerization, the clamps are removed, which press the pouring plates 651, 652 against the sample plate, and the sample plate 601 is ready for use.

Electrophoretic optical analysis:
102) In the analysis area, a sample plate 601 with poured gel channels is inserted into the station T, the upper analysis plate 622 is closed (manually).
103) The upper analysis plate 622 is pressed on, e.g. pneumatically, for sealing.
104) A small amount of buffer solution is filled into the chambers 625 from a capillary.
105) Analyte is filled (manually) into the loading dents by means of a pipette.
106) The remaining buffer solution is filled into the chambers 625 from a capillary.
107) An adequate high voltage is applied to the electrodes 627, the analyte is separated.
108) After completion of the separation, the remaining buffer solution is sucked off.
109) The upper analysis plate 622 is loosened, the sample plate 601 is displaced in the station F, and the upper analysis plate 632 is pressed on.
110) Stain liquid is directed into a thermostatic chamber from a reservoir.
111) The chambers 635 and 636 as well as the gel channels 602 are rinsed in circulation with tempered stain liquid from the thermostatic chamber.
112) The stain liquid is disposed into an effluent container.
113) From a reservoir, stain liquid is directed to a thermostatic chamber.
114) From the thermostatic chamber, the chambers 635 and 636 as well as the gel channel 602 are rinsed in circulation with tempered de-staining liquid.
115) The de-staining liquid is disposed into an effluent container.
116) The light sources 637 are switched on.
117) The detector 639 is read out.
118) The data is transmitted to the computer connected thereto.
119) The chambers involved are rinsed with water.
120) The analysis plate 632 is loosened.
121) The analysis plate 632 is folded upwards, the sample plate is removed (manually).

Electrophoretic immunologic analysis, blotting:
122) In the analysis area, a blotting membrane 649 is introduced into the plunger 644 (manually).
123) A sample plate 601 with poured gel channels is inserted into the station T, the upper analysis plate 622 is closed (manually).
124) The upper analysis plate 622 is pressed on, e.g. pneumatically, for sealing.
125) From a capillary, a small amount buffer solution is filled into the chambers 625.
126) By means of a pipette, analyte is filled into the loading dents 626 (manually).
127) From a capillary, the remaining buffer solution is filled into the chambers 625.
128) An adequate high voltage is supplied to the electrodes 627, the analyte is separated.
129) After completion of the separation, the remaining buffer solution is sucked off.
130) The upper analysis plate 622 is loosened, the sample plate 601 is displaced into station B and the upper analysis plate 642 is pressed on.
131) The plunger 644 with the membrane plate 610 is pressed against the sample plate 601.
132) From a reservoir, blotting buffer is directed into a thermostatic chamber.
133) From the thermostatic chamber, the chambers 645 and 646 as well as the gel channels 602 are filled with tempered blotting liquid.
134) By means of a slight negative pressure in the chamber 647, it is ensured that the membrane is soaked with buffer.
135) An adequate high voltage is applied to the electrodes 647 and 648, the separated analyte is transferred into the membrane 649.
136) After completion of the blotting, the upper analysis plate 642 is loosened.
137) The analysis plate 642 is folded upwards, the sample plate 601 is removed (manually).
138) The blotting membrane 649 is removed (manually).

The membrane can be further processed in the apparatus after blotting, or conventionally outside the apparatus.

The procedure of immune reaction during the electrophoretic immunologic analysis differs according to the problem to be solved. Principally, three steps can be distinguished which are repeated multiply in alternating sequence with different liquids:

A) applying immune reagent.
B) rinsing membrane.
C) Detecting.

Additionally, there are differences according to embodiment VI or VII.

Embodiment VI, Applying Immune Reagent:

139) In the station R of the immune area, the blotting membrane 649 from the preceding working step is inserted into a membrane plate 610 (manually).
140) The analysis plate 672 is closed (manually).
141) The upper analysis plate 672 is pressed on, e.g. pneumatically, for sealing.

142) Immune reagent is filled into the reagent wells 675 from a pipette (manually).
143) The immune reaction takes place.

Embodiment VI, Rinsing:

b 144) The upper analysis plate 672 is loosened, the sample plate 601 is displaced into station W, and the upper analysis plate 682 is pressed on.
145) From a reservoir, washing liquid is directed into a thermostatic chamber.
146) From the thermostatic chamber, the chambers 685 and 686 and the blotting membrane 649 are rinsed in circulation with tempered washing liquid.
147) Washing liquid is disposed into an effluent container.
148) The chambers involved are rinsed with water.

Embodiment VI, Detecting:

149) The upper analysis plate 682 is loosened, the membrane plate 610 is displaced into station D, and the upper analysis plate 692 is pressed on.
150) The light sources 697 are switched on.
151) The detector 699 is read out.
152) The data is transmitted to the computer connected thereto.
153) The analysis plate 692 is loosened.
154) The analysis plate 692 is folded upwards, the membrane plate 610 is removed (manually).

Embodiment VII, Applying Immune Reagent:

155) The sample plate is removed. In the station B of the analysis area, the blotting membrane 649 from the preceding working step is/remains inserted into the membrane plate 610 (manually).
156) The analysis plate 642 is closed (manually).
157) The plunger 644 presses on the membrane 649 for sealing, e.g. pneumatically.
158) The external plane 643 of the upper analysis plate is opened (manually).
159) Immune reagent is filled into the reagent wells 675 from a pipette (manually).
160) The external plane 643 of the upper analysis plate is closed (manually).
161) The immune reaction takes place.
162) The remaining immune reagent is sucked off via the chamber 645.

Embodiment VII, Rinsing:

163) From a reservoir, washing liquid is directed into a thermostatic chamber.
164) From the thermostatic chamber, the chambers 645 and 646 and the blotting membrane 649 are rinsed in circulation with tempered washing liquid.
165) The washing liquid is disposed into an effluent container.
166) The chambers involved are rinsed with water.

Embodiment VII, Detecting:

167) The plunger 644 is loosened.
168) The detector plate is slid laterally between membrane plate 610 and the upper analysis plate 642.
169) The plunger 644 is pressed on.
170) The light sources of the detector plate are switched on.
171) The detector of the detector plate is read out.
172) The data is transmitted to the computer connected thereto.
173) The plunger 644 is loosened.
174) The detector plate is removed sideward.
175) The analysis plate 642 is folded upwards, the membrane plate 610 is removed (manually).

The invention also comprises a component of a device for separation and detection of test substances, as proteins, nucleic acid fragments or similar substances, having at least one channel, whereby in a direction A such channel is substantially more extended as in the two other directions B and C; the channel is filled with matrix, and the channel is loaded with test substance at an end of the direction A, and the channel being contacted electrically at both ends of the direction A for separation of the test substances, and the channel being covered translucently in at least one direction B1, being perpendicular to the direction A, and enabling the determination of the position of the test substances after the separation from said direction B1, and the channel lying open over approximately the entire length in at least a further direction C1, perpendicular to direction A, and enabling the matrix to be rinsed in the channel with the separated test substance simultaneously on approximately the entire length from said direction C1 with liquids, without changing the position of the matrix in the component.

The channel can be completely or partially free in a further direction C2, which is opposite to the direction C1.

Said direction C1 in which the channel is free/open, hereby can be perpendicular to said direction B1, in which the position of the separated test substances is determined.

In a further direction B2, being opposite to the direction B1, the channel can be covered translucently, and in the combination with the direction B1, transmission measurements can be possible. The extension of the channel in direction A can be between 5 and 250 mm; the extension of the channel in the directions B and C can be between 0.01 and 10 mm. The position of the separated test substance can be determined by the changes of the transmission or reflection or emission or conversion of the light or the emission of radioactive radiation or the conductivity or the pH-value.

The separation of the test substances can result electrophoretically by applying a current in direction A.

The separation of the test substances can also result from isoelectric focusing under applying a current in direction A.

In direction C1 and/or C2, a membrane can be pressed against the matrix and by a further current and/or by a pressure difference and/or by a concentration gradient, the test substance can be transferred onto this membrane. In direction C1 and/or C2, said matrix can be pressed against a further matrix with the front, and the test substance can be transferred to said second matrix by a further current.

The channel can be accommodated in a rigid carrier, enabling the channel to be closed watertight temporarily limited in the direction C1 and C2, respectively, transverse to the plates by means of sealing elements, and the channel can be accessible for liquids and the two ends of direction A by adequate shaping of said carrier, without influencing the lateral sealing elements, and the channel can be contacted electrically via said liquid.

The component mentioned can be formed such that the channel is arranged in direction B1 and B2, respectively, between two optically translucent plates with high mechanical rigidity, enabling the channel to be closed watertight temporarily limited in the direction C1 and C2, respectively, transverse to the plates by means of sealing elements, and the channel can be accessible for liquids at the two ends of direction A by means of adequate end pieces, without influencing the lateral sealing elements, and the channel can be connected electrically via said liquid.

Said plates can be extended substantially wider in the direction facing away from the channel, as it would correspond to a thickness of the plates and the thickness of the channel. One or both of said sealing elements can be accommodated in the sealed chambers, enabling the supply of liquids to the channel from one or both sides. Said channel can be accommodated in the plate as a slot. Said plate can be optically translucent. Said channel can terminate at both ends within said plate, and can be accessible for liquids from the plane for a perpendicular to the plate. In said plate, one or two optical elements can be accommodated, deflecting the optical path from the plate plane in a direction perpendicular thereto. Said plate can be composed of two parts, being separated along the slot. Said optical elements can be inserted in that said plate can be separated at 45°, metallized and reassembled. Said plate can be that plane such that said slot can be sealed by further plates which are pressed from both sides two-dimensionally.

The component mentioned, can be designed such that further slots are accommodated within said plate, running transverse to said channel; further, also such that two or several plates can be connected to each other such that all plates can be moved together.

The invention also comprises a mechanism for transport of substances or materials between processing stations, whereby one or more cavities are arranged in a plate, the sample plate, which is substantially thinner than wide or long, and said cavities, can be opened towards one or both faces of the sample plate, and said sample plate being arranged displaceable between two further plates, the analysis plates, which close all or parts of the cavities of the sample plates by temporarily pressing on, and adequate sensors and/or manipulators being arranged at two or several stations at the analysis plates, affecting the cavities and/or other parts of the plate, and/or their content, and, or detect these. The cavities hereby can be slots, preferentially running transverse to the transport direction. All or part of said cavities can be filled completely or partially with gel matrix.

In the cavities, test substances as proteins, nucleic acid fragments, or similar substances can be transported. The sample plate can also be connected to further sample plates of similar or equal constructions such that all sample plates can be displaced to the different stations together.

Further the invention comprises a displaceable sample plate for a transport mechanism whereby optical elements are embedded into the sample plate, allowing for the observation of the content of the cavities in the surface of the sample plates from a position perpendicular to the sample plates. In the sample plate, penetrations can be embedded, allowing for the cleaning of the capillaries in the stations. In the sample plate, one or several vats of similar length as said slots can be embedded; having a lower depth than the thickness of said analysis plate. The vats can be provided with a penetration in the bottom surface, comprising the bottom area completely or partially. The vats can be adequate for receiving and the transport of a membrane.

The invention also comprises a station for the transport mechanism mentioned above, whereby non-polymerized electrophoresis matrix is filled in one or several of the cavities of the sample plate from capillaries. Hereby, adequate elements and penetrations can be arranged allowing for the loading of the matrix with test substance, and/or the filling of electrolysis buffer, and/or the electrophoretic separation, and/or the separation by means of isoelectric focusing and/or the optical detection of the running front.

Adequate elements and penetrations can be arranged, allowing for the staining and/or de-staining of the matrix, and/or the optical evaluation of the electrophoresis image by means of the optical elements integrated into the sample plate. Adequate elements and penetrations can be arranged, allowing for the evaluation of the electrophoresis image in the matrix by means of light transmission or light reflection or light emission or fluorescence or radio active radiation or other methods. Adequate elements and penetrations can be arranged, allowing for the transfer of the separated test substance into a membrane by means of current, and/or pressure difference, and/or by a concentration gradient. Adequate elements and penetrations can be arranged, allowing for the transfer of the separated test substance into a matrix plate by means of current, in which further electrophoresis can take place in a direction perpendicular to the direction of the first electrophoresis.

The station for a transport mechanism can also be designed such that a membrane can be deposited in a vat of the sample plate for transport. The station for a transport mechanism also can further be designed such that a membrane in a vat of the sample plate can be brought into contact with a liquid from one and/or two sides on the entire length or a sub-area of a membrane. Liquid can be pressed through the entire length or a sub-area of a membrane, lying in a vat of the sample plate, on both sides by means of a pressure difference. A membrane can also be analyzed with respect to the products of an immune reaction, and, in fact, by means of measurement of the transmission or reflection or emission or conversion of light, or the emission of radio active radiation, or the conductivity, or the pH-value.

LIST OF REFERENCE NUMERALS 1 sample plate
2 gel channel, separation chamber
3 mirror
4 slot
5 slot/vat/dent
8 lower analysis plate
9 upper analysis plate
10 inlet
11 outlet
12 inlet
13 outlet
14 plunger
20 funnel
21 funnel
22 heat exchanger
30 chamber
31 chamber
32 heat exchanger
33 heat exchanger
34 detector
35 lens
36 light source
37 light source
40 membrane
41 plunger
42 vat
43 chamber
44 heat exchanger
50 chamber
51 vat
60 sensor 61 lens
101 separation chamber/gel channel
102 glass pate/support element
103 glass plate/support element
104 chamber
105 chamber
106 end piece/outlet opening
107 end piece/funnel
110 plate
111 sealing
112 rod/plunger
120 plate
121 sealing
122 rod/plunger
124 cover
130 sensor
132 light source
133 mirror
210 end plate
211 wing
212 wing
213 end plate
214 gel channel
215 glass plate/support elements
216 wing
217 wing
224 capillary
225 sealing vat of the main apparatus
226 sealing vat of the main apparatus
227 liquid inlet of the main apparatus
228 liquid inlet of the main apparatus
230 chamber of the carrier
231 chamber of the carrier
232 reservoir
233 tank
240 plunger
241 blotting membrane
242 channel of the plunger
310 end plate of the carrier
311 wing
312 wing
313 end plate of the sticks
314 gel channel
315 glass plate/support element
316 wing
317 wing
321 sealing plates of the main apparatus
322 sealing plates of the main apparatus
327 terminals of the main apparatus
328 terminals of the main apparatus
329 capillary
330 chamber of the carrier
331 chamber of the carrier
332 reservoir
333 tank
334 viewing access to the gel channel
335 viewing access to the gel channel
601 sample plate
602 gel channel, separation chamber
603 mirror
604 spacer
605 holder
606 holder
610 membrane plate
621 lower analysis plate
622 upper analysis plate
623 upper analysis plate $2^{nd}$ layer
625 vat
626 sample well
627 electrode
628 electrode
631 lower analysis plate
632 upper analysis plate
634 upper analysis plate $2^{nd}$ layer
635 chamber
636 chamber
637 light source
638 mirror
639 detector
641 lower analysis plate
642 upper analysis plate
643 upper analysis plate $2^{nd}$ layer
644 blotting plunger
645 chamber
646 chamber
647 electrode
648 electrode
649 membrane
651 pouring plate
652 pouring plate
653 auxiliary plate
654 auxiliary plate
655 inlet
656 inlet
657 inlet
658 slider
659 slider
660 slider
671 lower analysis plate
672 upper analysis plate
675 reagent well
681 lower analysis plate
682 upper analysis plate
683 upper analysis plate $2^{nd}$ layer
684 lower analysis plate $2^{nd}$ layer
685 chamber
691 lower analysis plate
692 upper analysis plate
697 light source
698 mirror
699 detector

The invention claimed is:

1. Device for automatic analysis of the components of at least one analyte, by means of at least one of gel electrophoresis and isoelectric focussing,
for use with at least one separation matrix,
wherein the device comprises at least one support element and defines at least one transfer chamber;
wherein the support element is adapted to carry the separation matrix in a support direction, on at least one side, such that the separation matrix is loadable with an analyte and is contactable electrically at opposite ends in a separation direction for separation of the analyte into its components;
wherein the device is adapted to allow a mass transfer process with the transfer chamber, from one side in an access direction, over substantially the entire area of the separation matrix, in which the components of the analyte are contained after separation,
wherein the support element has a continuous sealing face to the transfer chamber, wherein the sealing face substantially prevents the mass transfer process outside the area of the separation matrix, wherein the access direction is different than the support direction and the separation direction, and wherein the support element is adapted to be fixed to the separation matrix during separation and transfer.

2. Device according to claim 1, wherein the support element is adapted to carry a separate separation matrix for each said at least one analyte.

3. Device according claim 1, further comprising means for electrical contact of the separation matrix on both sides of the access direction, for transfer of the separated components of the analyte onto a membrane.

4. Device according to claim 1, further comprising means for measurement of reflection or transmission of the separation matrix in at least one of the access direction and the support direction.

5. Device according to claim 1, wherein the support element is further adapted to delimit the at least one separation matrix on both sides in the support direction.

6. Device according to claim 1, wherein the separation direction, the support direction, and the access direction are substantially perpendicular with respect to each other.

7. Device according claim 1, wherein the support element is further adapted to carry at least one additional separation matrix in contact with the at least one separation matrix, into which the components of the analyte can be transferred.

8. Device according to claim 1, further comprising a membrane that can be brought into contact with the at least one separation matrix in the access direction, onto which the components of the analyte can be transferred.

9. Device according to claim 1, further comprising one of a penetration and a channel disposed in the at least one support element transverse with respect to the separation direction, allowing for the mass transfer with the at least one separation matrix, and adapted for primary separation of the analyte.

10. Device for automatic analysis of the components of at least one analyte, by means of at least one of gel electrophoresis and isoelectric focussing, for use with at least one separation matrix, the device comprising a support element, wherein the support element is adapted to carry the separation matrix in a support direction, on at least one side, such that the separation matrix is loadable with an analyte, and is contactable electrically at opposite ends in a separation direction for separation of the analyte into its components, wherein the support element is adapted to allow a mass transfer process, from both sides in an access directions, over substantially the entire area of the separation matrix, in which the components of the analyte are contained after separation, wherein the support element on both sides in the access direction has a continuous sealing face, substantially preventing the mass transfer process outside the area of the separation matrix, and wherein the access direction is different than the support direction and the separation direction.

11. Method for automatic analysis of the components of at least one analyte, by means of at least one of gel electrophoresis and isoelectric focussing, using at least one separation matrix, wherein each said separation matrix
is carried, in a support direction, on at least one side by a support element,
is loaded with an analyte, and
is contacted electrically at opposite ends in a separation direction for
separation of the analyte into its components, the method comprising:
carrying out a mass transfer process from one side in an access direction,
over substantially the entire area of the separation matrix containing the components of the analyte after separation,
wherein the access direction is different than the support direction and the separation direction,
wherein the support element has a continuous sealing face with a transfer chamber, substantially preventing the mass transfer process outside the area of the separation matrix, and
wherein the separation matrix is fixed to the support element during separation and transfer.

12. Method according to claim 11, further comprising providing electrical contacts on both sides of the separation matrix in the access direction, for transfer of the separated components of the analyte onto a membrane.

13. Method according to claim 11, further comprising carrying out a mass transfer process from both sides of the access direction with the separation matrix.

* * * * *